United States Patent [19]
della-Cioppa et al.

[11] Patent Number: 5,529,909
[45] Date of Patent: Jun. 25, 1996

[54] TYROSINASE-ACTIVATOR PROTEIN FUSION ENZYME

[75] Inventors: Guy della-Cioppa, Vacaville; Monto Kumagai, Davis, both of Calif.

[73] Assignee: Biosource Technologies, Inc., Vacaville, Calif.

[21] Appl. No.: 152,483

[22] Filed: Nov. 12, 1993

Related U.S. Application Data

[63] Continuation-in-part of Ser. No. 857,602, Mar. 30, 1992, and Ser. No. 923,692, Jul. 31, 1992, Pat. No. 5,316,931, which is a continuation-in-part of Ser. No. 600,244, Oct. 22, 1990, abandoned, Ser. No. 641,617, Jan. 16, 1991, abandoned, and Ser. No. 737,899, Jul. 26, 1991, abandoned, which is a continuation of Ser. No. 363,138, Jun. 8, 1989, abandoned, which is a continuation-in-part of Ser. No. 219,279, Jul. 15, 1988, abandoned, said Ser. No. 600,244, is a continuation of Ser. No. 310,881, Feb. 17, 1989, abandoned, which is a continuation-in-part of Ser. No. 160,766, Feb. 26, 1988, abandoned, and Ser. No. 160,771, Feb. 26, 1988, abandoned, said Ser. No. 641,617, is a continuation of Ser. No. 347,637, May 5, 1989, abandoned.

[51] Int. Cl.[6] .................. C12N 9/02; C12N 1/20; C12N 15/53; C12N 15/62
[52] U.S. Cl. .............. 435/69.7; 536/23.4; 536/23.2; 435/320.1; 435/189; 435/252.3; 435/252.33; 435/252.35; 935/47
[58] Field of Search .................. 536/23.2, 23.4; 435/320.1, 189, 69.7, 252.3, 252.35, 252.33; 935/47

[56] References Cited

U.S. PATENT DOCUMENTS 4,898,814  2/1990  Kwon ............................................ 435/6

OTHER PUBLICATIONS

Huber, et al., *Nuc. Acids Res.*, vol. 15, No. 19, 1987, p. 8106.
Bernan, et al., *Gene*, vol. 37, 1985, pp. 101–110.
Lee, et al., *Gene*, vol. 65, 1988, pp. 71–81.
Huber, et al., *Biochem.*, vol. 24, 1985, pp. 6038–6044.

*Primary Examiner*—Robert A. Wax
*Assistant Examiner*—Keith D. Hendricks
*Attorney, Agent, or Firm*—Albert P. Halluin; Pennie & Edmonds

[57] ABSTRACT

The present invention relates to a nucleic acid sequence that encodes a fusion enzyme of tyrosinase and a tyrosinase activator protein. Further, the present invention also relates to the amino acid sequence which is encoded by the nucleic acid sequence of the fusion enzyme. The fusion enzyme may also include a linker positioned between the amino acid sequences of the tyrosinase and the tyrosinase activator protein. Still further, the present invention also relates to a vector useful for introducing the nucleic acid sequence encoding the fusion enzyme into an organism. Still further, the present invention relates to melanins made by the fusion enzyme and a method for making melanins using the fusion enzyme.

57 Claims, 7 Drawing Sheets

TYROSINASE-ACTIVATOR PROTEIN FUSION ENZYME

This application is a continuation in part of application Ser. No. 7/857,602, filed Mar. 30, 1992 pending. This application is also a continuation-in-part of application serial No. 923,692 filed Jul. 31, 1992 now U.S. Pat. No. 5,316,931 which is a continuation-in-part of applications Ser. No. 600,244, filed Oct. 22, 1990, Ser. No. 641,617, filed Jan. 16, 1991, and Ser. No. 737,899 filed Jul. 26, 1991. all abandoned Ser. No. 600,244 is a continuation of application Ser. No. 310,881, filed Feb. 17, 1989, now abandoned, which is a continuation-in-part of applications Ser. No. 160,766 and 160,771, both filed on Feb. 26, 1988 and now abandoned. Ser. No. 641,617 is a continuation of application Ser. No. 347,637, filed May 5, 1989, now abandoned. Ser. No. 737,899 is a continuation of application Ser. No. 363,138, filed Jun. 8, 1989, now abandoned, which is a continuation-in-part of application Ser. No. 219,279, filed Jul. 15, 1988 and now abandoned. The disclosures of all of the foregoing are incorporated by reference.

BACKGROUND OF INVENTION

Melanogenesis, production of the biological polymer melanin, is a widespread phenomena in nature occurring in most phyla from fungi to mammals. The black, brown, buff and Tyndall-blue pigments found in feathers, hairs, eyes, insect cuticle, fruit and seeds are usually melanins. Melanins have been assigned a photoprotective role in the skin, their role in the eye and inner ear is unknown. Melanins are also found in the mammalian brain where they are referred to as neuromelanins. The biological function of neuromelanins is unknown.

The stepwise biosynthesis of melanins is depicted in FIG. 1. Tyrosinase (E. C. 1.14.18.1) catalyzes two types of reactions involved in the biosynthesis of melanin: the ortho-hydroxylation of monophenols to catechols, which is referred to as cresolase activity, and the dehydrogenation of catechols to o-quinones, designated as catecholase activity. Molecular oxygen is used for the hydroxylation reaction. For this reason, tyrosinase acting on a monophenol is referred to as a "mixed function oxidase". Hayaishi, in "Biological Oxidation" (Singer, ed.) p.581, Interscience Publishers, New York (1968). As used herein tyrosinase refers to all enzymes possessing the above described enzymatic activity. Tyrosinases are also sometimes referred to as polyphenol oxidases.

As can be seen from the biosynthetic pathway of melanin depicted in FIG. 1, tyrosinase is essential to the production of melanin. Therefore, the ability of an organism to express significant quantities of tyrosinase activity is essential to the organism's in vivo production of melanin.

Tyrosinase is not naturally found in all organisms. Rather, tyrosinase has been found to occur in a relatively limited number of prokaryotes, is absent in a variety of higher plants and is generally confined to specific cells of the skin in higher animals but may also occur in interior tissue, such as the substantia nigra, eye and inner ear. Given the limited number of organisms that produce melanin, one objective of the present invention is to provide a means for introducing tyrosinase activity into organisms that are otherwise unable to produce melanin.

Even in those organisms where tyrosinase activity occurs naturally, such activity is generally present at low levels. As a result, melanin is generally produced in small quantities by those organisms that possess tyrosinase activity. It is therefore a further objective of the present invention to provide a means for enhancing the level of tyrosinase activity in organisms in order to enhance the in vivo production of melanin.

Several prior art references teach how to genetically engineer an organism to possess tyrosinase activity. In U.S. application Ser. No. 7/857,602, filed Mar. 30, 1993, which is incorporated herein by reference, Applicants teach a method for producing melanin from transformed microorganisms wherein a sequence encoding for tyrosinase is introduced into the organism. Microorganisms that have be genetically engineered to enhance their abilities to produce tyrosinases include, but are not limited to species of Streptomyces, Escherichia, Bacillus, Streptococcus, Salmonella, Staphylococcus, and Vibrio. For example, cloned tyrosinase genes from *Steptomyces sp.* have been shown to produce melanin pigments in culture. *J. Gen. Microbiol.* 129:2703–2714 (1983); *Gene* 37:101–110 (1985). The cloned genes have also been expressed in *Streptomyces* and *E. coli.* dellaCioppa, *Bio/Technology* 8:634–638 (1990). In each case, both tyrosinase and ORF438 were required for melanin production.

U.S. Pat. No. 4,898,814 issued to Kwon discloses a cDNA clone of human tyrosinase and claims a method of making human tyrosinase by expressing the cDNA in *E. coli.*

Many forms of tyrosinase from bacteria, such as Streptomyces, require an activator protein. For example, the mel locus of *S. antibioticus* has been shown to contain two open reading frames (ORF's) that encode a putative ORF438 protein ($M_r$=14,754) and tyrosinase ($M_r$=30,612). ORF438 and tyrosinase are thought to be transcribed from the same promoter in *S. antibioticus.* Bernan, et al., *Gene* 37:101 (1985). Both genes are required for melanin production. Bernan, et al., *Gene* 37:101 (1985). Based on genetic evidence, ORF438 protein has been shown to function as a trans-activator of tyrosinase. Lee, et al., *Gene* 65:71 (1988). It has been suggested that the ORF438 protein is involved in tyrosinase secretion, or it may function as a metallothionein-like protein that delivers copper to tyrosinase, Bernan, et al., *Gene* 37:101 (1985); Lee, et al., *Gene* 65:71 (1988). The mel locus of *S. glaucescens* has a nearly identical ORF sequence upstream of tyrosinase that probably serves a similar function. Huber, et al. *Biochemistry.* 24:6038 (1985); Huber, et al., *Nucleic Acids Res.* 15:8106 (1987). The existence of an ORF438 protein, however, has never been confirmed in vivo.

The melanin operons of *S. antibioticus* and *S. glaucescens* have been isolated and sequenced, and both share sequence homology and similar gene arrangement. The polypeptide sequence encoded by ORF438 (146 amino acids) in *S. antibioticus* is structurally and functionally equivalent to URF402 (134 amino acids) from *S. glaucesecens* Huber, et al. *Nucleic Acids Res.* 15:8106 (1987). Disruption of the URF402 coding sequence abolishes the melanin phenotype similar to that already known for ORF438. Recent evidence suggest that the ORF438 protein (and by analogy the URF402 protein equivalent) functions as a molecular chaperone for tyrosinase. Chen, et al., *J. Biol Chem.* 268:18710 (1993).

Tyrosinase has also been isolated and employed to produce melanin in vitro. For example, in U.S. application Ser. No. 7/982,095, filed Nov. 25, 1992, which is incorporated herein by reference, Applicants teach the production of melanin in vitro using a tyrosinase which is excreted from the microorganism during fermentation. In vitro production of melanin is dependant on the production of significant quantities of tyrosinase activity. Tyrosinase activity may be lost during isolation of the secreted tyrosinase due to a disruption of the tyrosinase—activator protein complex. It is therefore an objective of the present invention to stabilize the tyrosinase—activator protein complex in order to reduce tyrosinase activity loss during isolation and purification.

Fusion proteins have been synthesized to overcome instability and proteolytic degradation of a polypeptide of interest. Many eucaryotic proteins have been produced in E. coli as fusion proteins with E. coli polypeptides such as Beta-galactosidase. Beta-galactosidase can be used to protect the foreign passenger protein from degradation in E. coli. Somatostatin, the first eurcaryotic protein to be produced in E. coli was produced by fusing a synthetic gene to the entire Beta-galactosidase coding sequence (Itakura, et al., Science 198:1056 (1977)) and somatostatin was subsequently isolated by chemical cleavage of the fusion protein. When two independently funtioning polypeptides are fused into a single polyprotein by way of a synthetic gene fusion, the resulting gene construct can be engineered for expression behind a single promoter, ribosome binding site, and initiation codon. A gene fusion constructed in such a way can be placed in a single location within a chromosome or episomal element for subsequent expression of the fusion protein. Such fusion genes are inherently more stable because both gene sequences are coordinately expressed at high levels from a single promoter. Undesirable effects such as differential down regulation or rearrangement and deletion of one of the genes can thus be avoided.

Unfortunately, however, most fusion protein constructs are not functional. Proteins fold into conformationally active states as dictated by their primary amino acid sequence. Additional polypeptide sequences at the C- or N- terminus can interfere with proper folding, thereby preventing the formation of a biologically active protein. Enzymes typically fold into well defined three-dimensional conformations to allow the formation of a catalytic pocket that excludes potential substrate molecules of abnormal size or conformation, but allows access of substrate molecules with the correct three-dimensional structure. Many enzymes will not function as fusion polypeptides because the sequence extensions interfere with proper folding, or interfere by sterically blocking the substrate's access to the catalytic site.

The present invention relates to Applicants' recognition that it might be possible to construct a biologically active fusion enzyme coupling tyrosinase with an activator protein. It has been shown that histidine residues #102 and # 117 of the ORF438 activator protein are critical for copper binding and delivery to the active site of tyrosinase. Chen, et al., J. Biol. Chem. 268:18710 (1993). In order to form a biologically active fusion enzyme between tyrosinase and an activator protein, both functional domains of tyrosinase and the activator protein must be correctly folded. Further, the fusion enzyme must be able to assume a structural conformation enabling the activator protein to intermolecularly deliver copper to the active site of the tyrosinase to form a biologically active tyrosinase. Based on the existing prior art, it is unclear whether such a fusion enzyme would be biologically active.

SUMMARY OF INVENTION

The present invention relates to a nucleic acid sequence encoding a fusion enzyme comprising a nucleic acid sequence encoding for a tyrosinase and a nucleic acid sequence encoding for a tyrosinase activator protein. Activator proteins used in the present invention include but are not limited to ORF438 and URF402. Tyrosinases used in the present invention include both prokaryotic and eucaryotic tyrosinases. Prokaryotic tyrosinases that require a separate activator protein, particularly tyrosinases derived from Streptomyces are preferred. It is also preferred that the activator protein sequence be positioned 5' relative to the tyrosinase sequence.

The present invention also relates to a vector useful for introducing a nucleic acid sequence encoding a fusion enzyme into an organism. The vector comprises a nucleic acid sequence encoding for a fusion enzyme of the present invention and a promoter sequence that regulates the transcription of fusion enzyme. The present invention also relates to organisms, such as bacteria, yeast fungi, plants and animals which have been transformed by the vector of the present invention.

The present invention also relates a fusion enzyme which comprises an amino acid sequence for tyrosinase and an amino acid sequence for a tyrosinase activator protein. The fusion enzyme may also contain a linker positioned between the amino acid sequences of the activator protein and the tyrosinase.

The present invention also relates to melanin produced by a fusion enzyme of the present invention. The melanin may be produced in vitro by contacting a fusion enzyme with an enzyme substrate under suitable reaction conditions to form melanin. Melanin may also be produced in vivo by an organism transformed with a vector of the present invention.

DETAILED DESCRIPTION OF THE INVENTION

Figure 1:
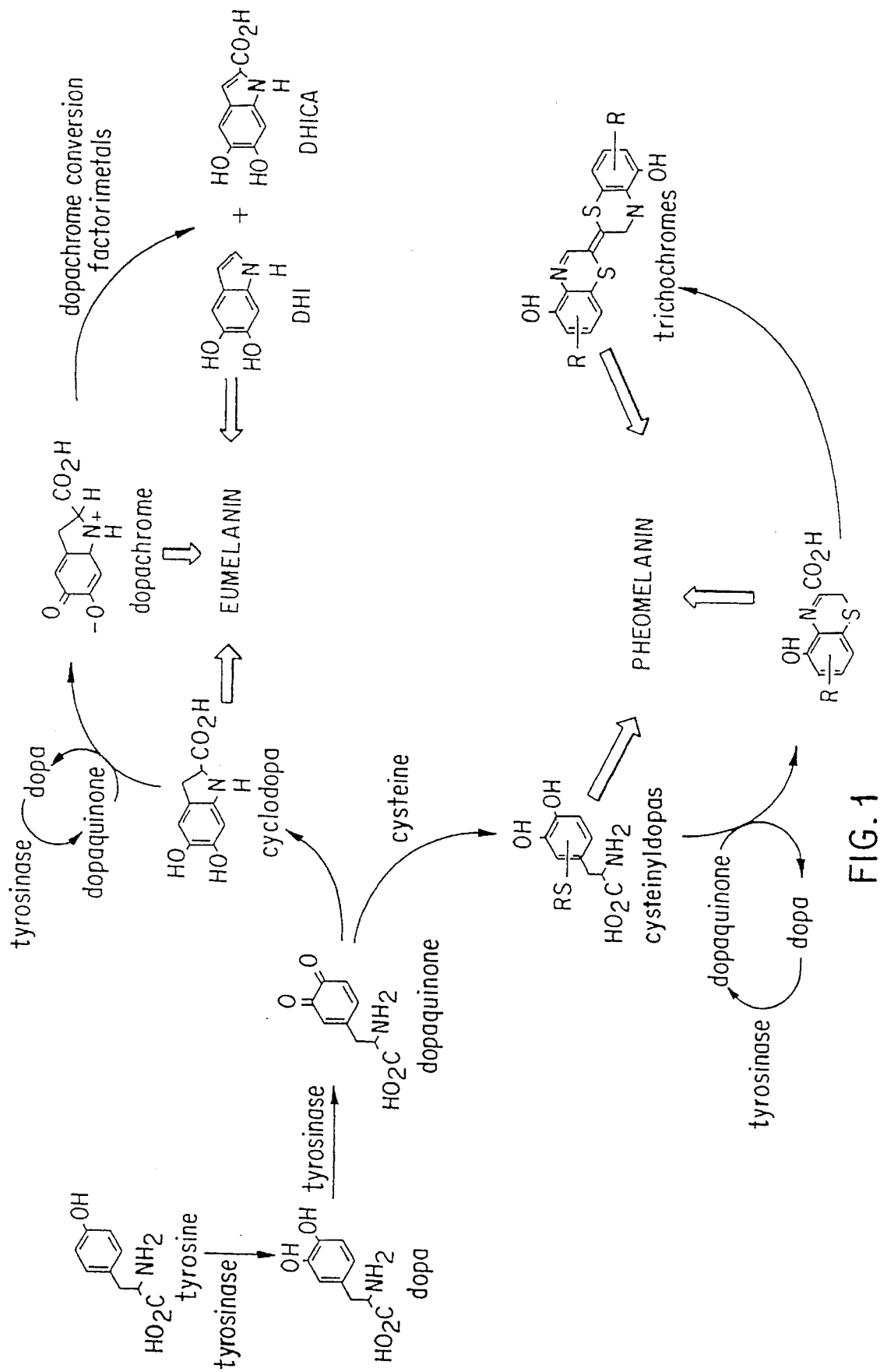
FIG. 1 depicts the stepwise biosynthesis of melanins.

The present invention relates to a nucleic acid sequence encoding for a fusion enzyme of tyrosinase and an activator protein for tyrosinase. The present invention also relates to a vector useful for transforming a host organism that contains the nucleic acid sequence of the present invention.

The present invention also relates to the expression of a fusion enzyme of a tyrosinase and an activator protein by the transformed organism. Host organisms that may be transformed to express the fusion enzyme of the present invention include but are not limited to bacteria, yeast fungi, plants and animals. Expression of the fusion enzyme by the host organism enables and/or enhances tyrosinase activity in the host thereby enabling and/or enhancing melanin production by the host.

The present invention also relates to a fusion enzyme comprising an amino acid sequence for tyrosinase and an amino acid sequence for an activator protein of tyrosinase.

Finally, the present invention relates to the in vivo and in vitro production of melanin using the fusion enzyme of the present invention.

The fusion enzyme of the present invention comprises an amino acid sequence for a tyrosinase and an amino acid sequence for an activator protein. The nucleic acid sequences for both proteins are under the same promoter control and are thus expressed as a single peptide.

Tyrosinases used in the present invention include both prokaryotic and eucaryotic tyrosinases. In some organisms, tyrosinases are referred to as polyphenol oxidases. Tyrosinases from prokaryotes are preferred, particularly those tyrosinases that require a separate activator protein such as those that have been obtained from Streptomyces.

Activator proteins used in the present invention include but are not limited to ORF438 and URF402. The activator protein employed in the present invention need not naturally occur in the organism from which the tyrosinase is derived. Rather, activator proteins from a variety of sources should function with a given tyrosinase in view of the similarity of the copper binding sites of different tyrosinases. See Chen, et al., *J. Biol. Chem.* 268 18710 (1993).

The fusion enzymes of the present invention are preferably constructed such that the amino acid sequence for the activator protein is positioned on the N- terminus of the tyrosinase amino acid sequence. As can be seen from Example 5, fusion enzymes where the activator protein is positioned on the N- terminus of tyrosinase exhibit equivalent melanin production capabilities as where tyrosinase and the activator protein are expressed separately.

Eucaryotic tyrosinases tend to comprise higher molecular weight (50–70 kD) single polypeptide chains without defined activator proteins. Applicants speculate that the activator equivalent of the ORF438. protein is built into the polypeptide backbone of eucaryotic tyrosinases. Based on the amino acid homology at the active sites between eucaryotic and Streptomyces tyrosinases, it appears that excess polypeptide sequences occur in the C- terminal region of the larger eucaryotic enzymes. Based on this observation, it might be predicted that ORF438 would function best if fused to the C- terminus rather than the N- terminus of the 30 kD Streptomyces tyrosinase since the fusion protein would then mimic the eucaryotic tyrosinases with respect to placement of the catalytic site. However, since many newly synthesized polypeptides undergo three dimensional folding into their preferred active conformation beginning with the free C- terminus, it might also be expected that C- terminal additions are disruptive to proper folding and, hence, normal catalytic activity. Hence, prior to preparing the fusion enzymes of the present invention, it was unclear whether a fusion enzyme at either the N- or C- terminus would be functional.

The amino acid sequence encoding the activator protein need not be directly attached to the tyrosinase sequence. In plasmid pBGC648, a His residue has been inserted between the activator protein and the tyrosinase sequence. A single amino acid and a repeating Pro-Thr amino acid sequence, which behaves as a natural hinge, are preferred as linking sequences between tyrosinase and the activator protein.

Determination of the wide variety of amino acid sequences that may be interposed between the tyrosinase and activator protein sequences can be routinely determined by one of ordinary skill in the art in view of the teachings of the present invention.

Other polypeptide linkers that are known from the literature to provide a high degree of flexibility between two polypeptide sub-domains might work equally as well as linking sequences between the tyrosinase sequence and the activator protein sequence. One example of this type of hinge polypeptide is a proline—threonine repeating unit such as those known form cellulose binding proteins. Ong, et al., *Bio/Technology* 7 604(1989). Construction of synthetic oligonucleotide linkers that encode hinge polypeptides of known flexibility is within the level of ordinary skill. In addition, synthetic oligonucleotide linkers could be used to construct random polypeptide linker sequences to join the tyrosinase—activator protein domains together. Linkers with a high degree of flexibility and sufficient length might be expected to work best for intermolecular cis-activation of tyrosinase. Inflexible linker polypeptides, or extremely short linker polypeptides, might be expected to permit only intramolecular trans-activation of neighboring fusion enzymes.

In order to provide a clear and consistent understanding of the specification and the claims, including the scope given to such terms, the following definitions are provided:

Activator protein: a gene product that alters, activates or enhances the activity of tyrosinase. The activator protein may function as a trans-activator, as a metallothionein-like protein that delivers an ion to a tyrosinase apoenzyme or it may function in assisting the secretion of tyrosinase. ORF438 gene, URF402 and ORF(s) 3' to the tyrosinase coding sequence code for activator proteins that enhance melanogenesis in all of the ways described.

Melanin: Melanins are polymers produced by polymerization of reactive intermediates. The polymerization mechanisms include but are not limited to autoxidation, enzyme catalyzed oxidation and free radical initiated polymerization. The reactive intermediates are produced chemically or enzymatically from precursors. Suitable enzymes include, but are not limited to peroxidase and catalases, polyphenol oxidases, tyrosinases, tyrosine hydroxylases or laccases. The precursors which are converted to the reactive intermediates are hydroxylated aromatic compounds. Suitable hydroxylated aromatic compounds include, but are not limited to 1) phenols, polyphenols, aminophenols and thiophenols of aromatic or polycyclic aromatic hydrocarbons, including but not limited to phenol, tyrosine, pyrogallol, 3-aminotyrosine, thiophenol and a-naphthol; 2) phenols, polyphenols, aminophenols, and thiophenols of aromatic heterocyclic or heteropolycyclic hydrocarbons such as but not limited to 2-hydroxypyrrole, 4-hydroxy-1,2-pyrazole, 4-hydroxypyridine, 8-hydroxyquinoline, and 4,5-dihydroxybenzothiazole. Suitable hydroxylated aromatic compounds also include X/L-tyrosine, L-tyrosine/X and X/L-tyrosine/X where X is a single amino acid, a dipeptide or an oligopeptide bound to L-tyrosine.

The nucleic acid sequences encoding for the fusion enzymes of the present invention may be inserted into a wide variety of vector constructs known in the art for transforming a host organism. Suitable techniques include those described in Maniatis, et al., *Molecular Cloning*, 1st Ed., Cold Spring Harbor Laboratory, New York (1982); *Molecular Cloning*, 2nd Ed., Cold Spring Harbor Laboratory, New York (1989); Methods in Enzymology, Vols. 68 (1979), 100 (1983), 101 (1983), 118 (1986) and Vols. 152–154 (1987) *DNA Cloning*, Glover, Ed., IRL Press, Oxford (1985); and *Plant Molecular Biology: Manual*, Gelvin, et al., Eds., Kluwer Academic Publishers, Podrecht (1988). Medium compositions have been described in Miller, Experiments in

*Molecular Genetics,* Cold Spring Harbor Laboratory, New York (1972), as well as the references previously identified. Hopewood, et al., "Genetic Manipulation of Streptomyces: A Laboratory Manual", The John Innes Foundation, Norwich, England (1985).

With regard to the expression of the tyrosinase-activator protein fusion enzyme of the present invention in a transformed microorganism, it is preferred that the transformed organism be grown under the conditions described in U.S. application Ser. No. 857,602, filed Mar. 30, 1992 which is incorporated herein by reference.

With regard to the expression of the tyrosinase-activator protein fusion enzyme of the present invention in plants, it is preferred that the nucleic acid cassette encoding the fusion enzyme be inserted into one of the viral constructs described in U.S. application Ser. No. 923,692, filed Jul. 31, 1992, or U.S. application Ser. No. 997,733, filed Dec. 30, 1992, which are both incorporated herein by reference.

Vectors encoding the tyrosinase-activator protein fusion enzyme of the present invention may be produced by standard techniques. Appropriate vectors which can be utilized as starting materials are known in the art.

The DNA sequence coding for the fusion enzyme is inserted into an appropriate vector in such a manner that the enzyme is correctly expressed. In other words, the DNA sequence is positioned in the proper orientation and reading frame so that the correct amino acid sequence is produced upon expression of the DNA sequence in the host. In accordance with conventional techniques, a chimeric DNA sequence is generally constructed which contains a promoter operable in the specific host and the DNA sequence coding for the desired enzyme. The chimeric DNA sequence may further contain 3' non-coding sequences operable in the host. The chimeric DNA sequence can be prepared in situ within a suitable vector by inserting the DNA sequence coding for the enzyme into a restriction site of a known host transformation vector. Alternatively, the chimeric gene could be first constructed and then inserted into a vector to produce a transformation vector. The vector can be further modified by utilizing an enhancer sequence and/or a strong promoter, which leads to an increased production of the fusion enzyme.

The typical vector is a plasmid having one or more marker genes for antibiotic resistance, an origin of replication, and a variety of useful restriction sites for cloning or subcloning restriction fragments. A large number of vectors have been described which are useful for transforming many microorganisms including but not limited to Streptomyces and *E. coli.* See, for example, *Cloning Vectors,* Pouwels, et al. ed. Elsevier Science Publishers Amsterdam (1985).

A large number of naturally occurring Streptomyces plasmids have been described, many of which are conjugally proficient. Two such isolates, SLP1.2 and pIJ101, have formed the basis of a series of useful plasmid vectors. Thompson, et al., *Gene* 20:51 (1982). The plasmids of the SLP1 family, of which SLP1.2 is the largest detected member, were discovered as autonomous replicons in *S. lividans* 66 after interspecific matings with *S. coelicolor* A3(2). The SLP1 replicon is integrated in the *S. coelicolor* genome but can be excised together with various lengths of neighboring DNA to become autonomous in *S. lividans.* The SLP1 plasmids exist stably at a copy number of 4–5 per chromosome in *S. lividans* and have a narrow host range.

The 8.9 kb plasmid pIJ101 was discovered in *S. lividans* ISP5434 (Kieser, et al., *Mol. Gen. Genet.* 185:223 (1982)) but can be conjugally transferred to a wide variety of Streptomyces species. Derivatives (e.g. pIJ102) have been isolated from the plasmid which have similar properties but are smaller. Kieser, et al. (1982), supra. Plasmid pIJ101 has a copy number of 100–300 per chromosome equivalent in most hosts and a minimum replicon of less than 2.1 kb. Derivatives carrying drug-resistance determinants have been constructed to act as vectors, and a chimeric plasmid which can be used as a shuttle vector between *E. coli* and Streptomyces is available.

The temperate phage φC31 has a wide host range within the Streptomycetes and lysogenizes *S. coelicolor* A-3(2) via a site-specific integration event. Lomovshaya, et al., *Bacteriol Rev.* 44, 206 (1980). Up to 42.4 kb of DNA can be packaged within a viable phage particle, but only 32 kb (at the most) of the DNA contains the genetic information essential for plaque formation. Derivatives of φC31 containing deletions can be used as vectors, and recombinant phages can either be grown lyrically or used to lysogenize suitable streptomyces strains.

pBR322-derived plasmids are very common for use in *E. coli* transformation. They possess a pair of antibiotic resistance genes which confer antibiotic resistance when *Escherichia coli* are successfully transformed. Typically, the insertion of a DNA segment is made so that one of the antibiotic resistance genes is inactivated. Selection then is accomplished by selecting for *E. coli* exhibiting antibiotic resistance conferred by the second gene. Bolivar, et al., *Gene* 2:95 (1977); and Sutcliff, J., *Proc. Natl. Acad. Sci,,* USA 75:3737 (1978).

Another example of transforming vectors is the bacteriophage. The M13 series are modified filamentous *E. coli* bacteriophage containing single stranded circular DNA. The M13 series carry the lacZ gene for β-galactosidase and will metabolize the galactose analog Xgal to produce a blue color. Placing a cloned insert into the polylinker sequence located in the amino terminus of the lacZ gene inactivates the gene. Microorganisms carrying an M13 with an inactivated lacZ (representing a cloned insert) are distinguishable from those carrying an M13 with an active lacZ gene by their lack of blue color. Messing, et al., *Proc. Natl., Acad. Sci., USA* 74:3642 (1977); and Messing, *Methods in Enzymology* 101:20 (1983).

Other transforming vectors are the pUC series of plasmids. They contain the ampicillin resistance gene and origin of replication from pBR322, and a portion of the lacZ gene of *E. coli.* The lac region contains a polylinker sequence of restriction endonuclease recognition sites identical to those in the M13 series. The pUC series have the advantage that they can be amplified by chloramphenicol. When a DNA fragment is cloned into the lac region the lac gene is inactivated. When *E. coli* containing a pUC plasmid with an inactivated lacZ gene is grown in the presence of isopropylthiogalactoside (IPTG) and 5-bromo-4-chloro-3-indolyl β-D-galactopyranoside (Xgal) its colonies are white. If it carries a pUC plasmid with an active lacZ gene its colonies are blue. Vieira, et al., *Gene* 19:259 (1982). Bacteria are transformed by means conventional in the art.

The genus Streptomyces is one of three aerobic genera of bacteria of the order Actinomycetales. Streptomyces are Gram-positive, mycelial, spore-forming bacteria. Several naturally occurring Streptomyces plasmids have been described. Streptomyces lividans TK64 has no tyrosinase gene and produces no melanin. Applicants teach the transformation of Streptomyces lividans TK64 with plasmid pIJ702 which encodes for the tyrosinase gene in U.S. application Ser. No. 7/857,602, filed Mar. 30, 1992 which is incorporated herein by reference. Transformation is carried out by means standard in the art. Similarly, transformation of Streptomyces can be performed using a plasmid encoding the fusion enzyme of the present invention. Transformation vectors of the present invention may also be used to transform a variety of microorganisms after insertion into vectors which are useful for transforming the corresponding host microorganism.

Bluescript (obtained from Stratagene, LaJolla, CA) is a pUC derivative having a β-galactosidase color indicator and a lac promoter. In U.S. application Ser. No. 7/857,602, Applicants teach modification of the Bluescript plasmid by inserting a tyrosinase gene. This modified plasmid was used to successfully transform *E. coli* which formed pigmented colonies. Similarly, the Bluescript may be modified by inserting a nucleic acid sequence encoding for the fusion enzyme of the present invention.

Melanin has been purified from bacterial cells with 0.5N NaOH at room temperature and at 100° C. Pigmented fractions were found to be: (1) soluble in acid and base; (2) soluble in ethyl alcohol and base; and (3) soluble base only. Pavlenko, et al., *Microbiology USSR* 50 539 (1981)

Soluble melanin can be extracted from the medium and purified. This is done by first removing cells and particulate matter using, for example, filtration or centrifugation. A variety of filtration methods are known in the art including filtration through glass wool. If centrifugation is used, 5,000× gravity is usually sufficient. The melanin is then precipitated at between pH 2–4, preferably about 3. Precipitated melanin is removed by either filtration or centrifugation. The melanin is washed by successive resolubilization at high pH, i.e. about pH 7.0 to about pH 9.0, preferably about pH 8.0, and precipitation at low pH followed by filtration or centrifugation. The melanin may also be concentrated using molecular weight filtration, such as reverse osmosis. Salt precipitation can be as effective in precipitating the melanin as low pH.

The invention is further illustrated by the following non-limiting examples.

EXAMPLES

1. Preparation of Plasmids pBGC623, pBGC635 and pBGC636

Figure 2:
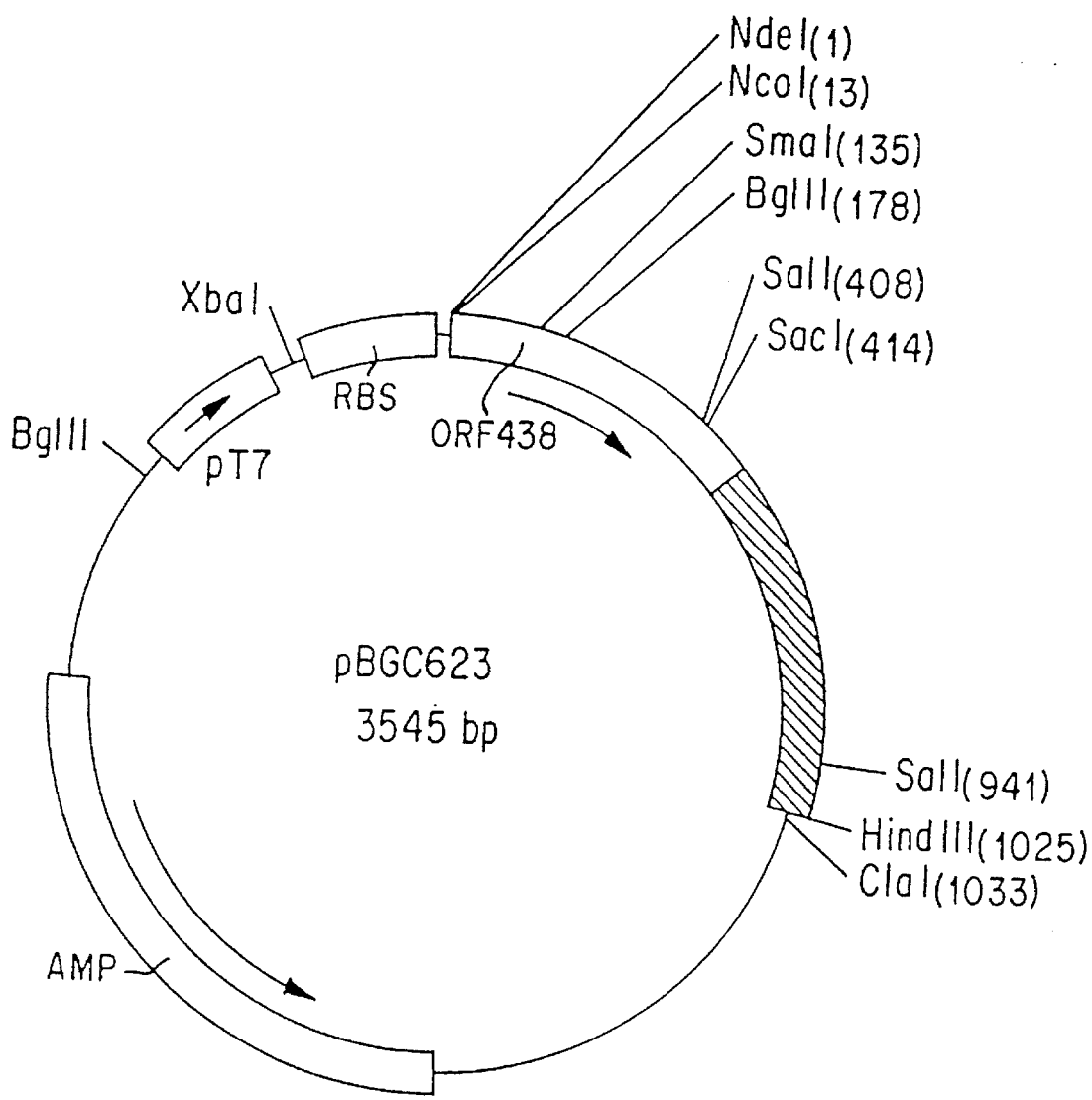
FIG. 2 provides the plasmid map of pBGC623.
Figure 3:
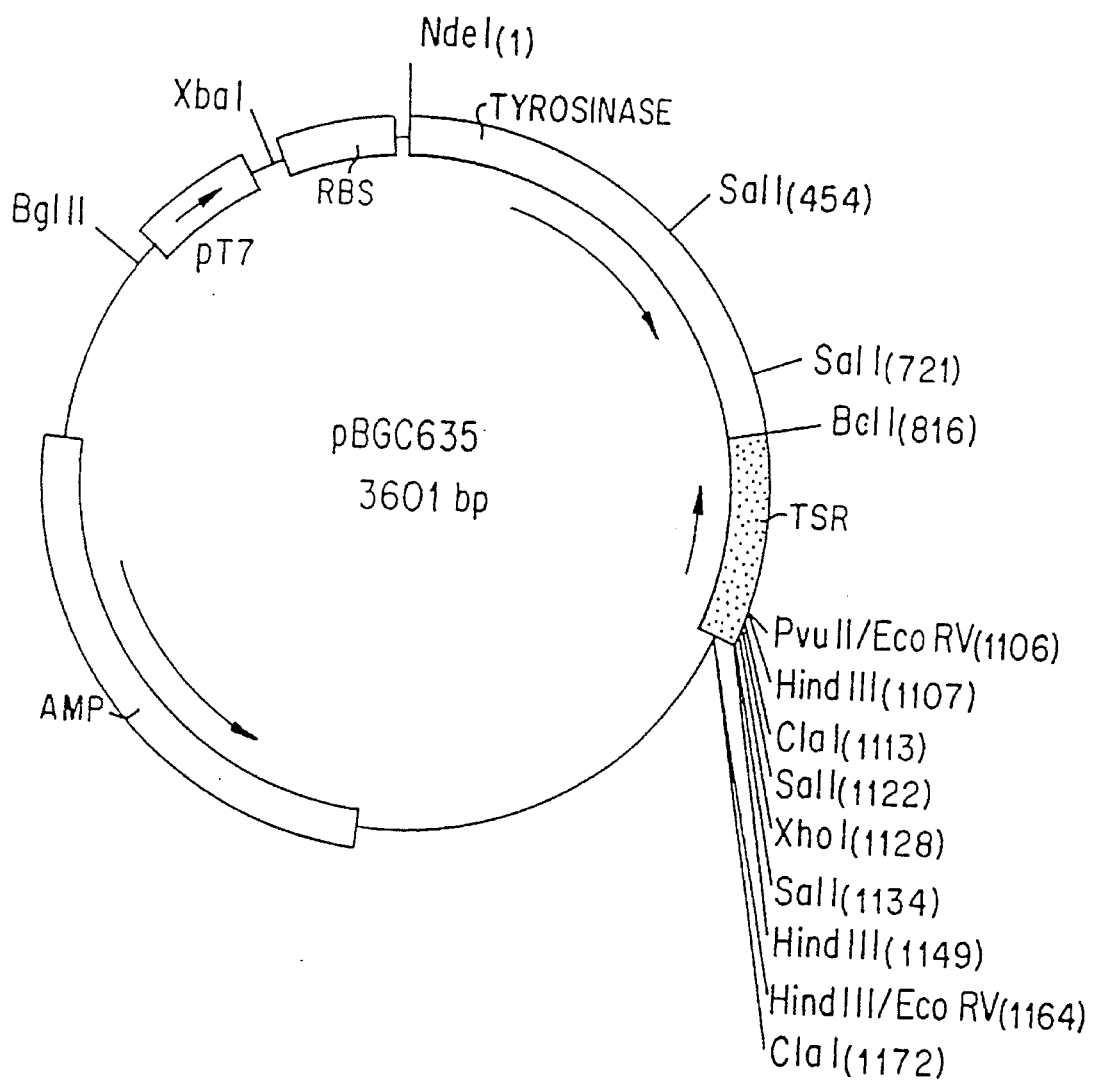
FIG. 3 provides the plasmid map of pBGC635.
Figure 4:
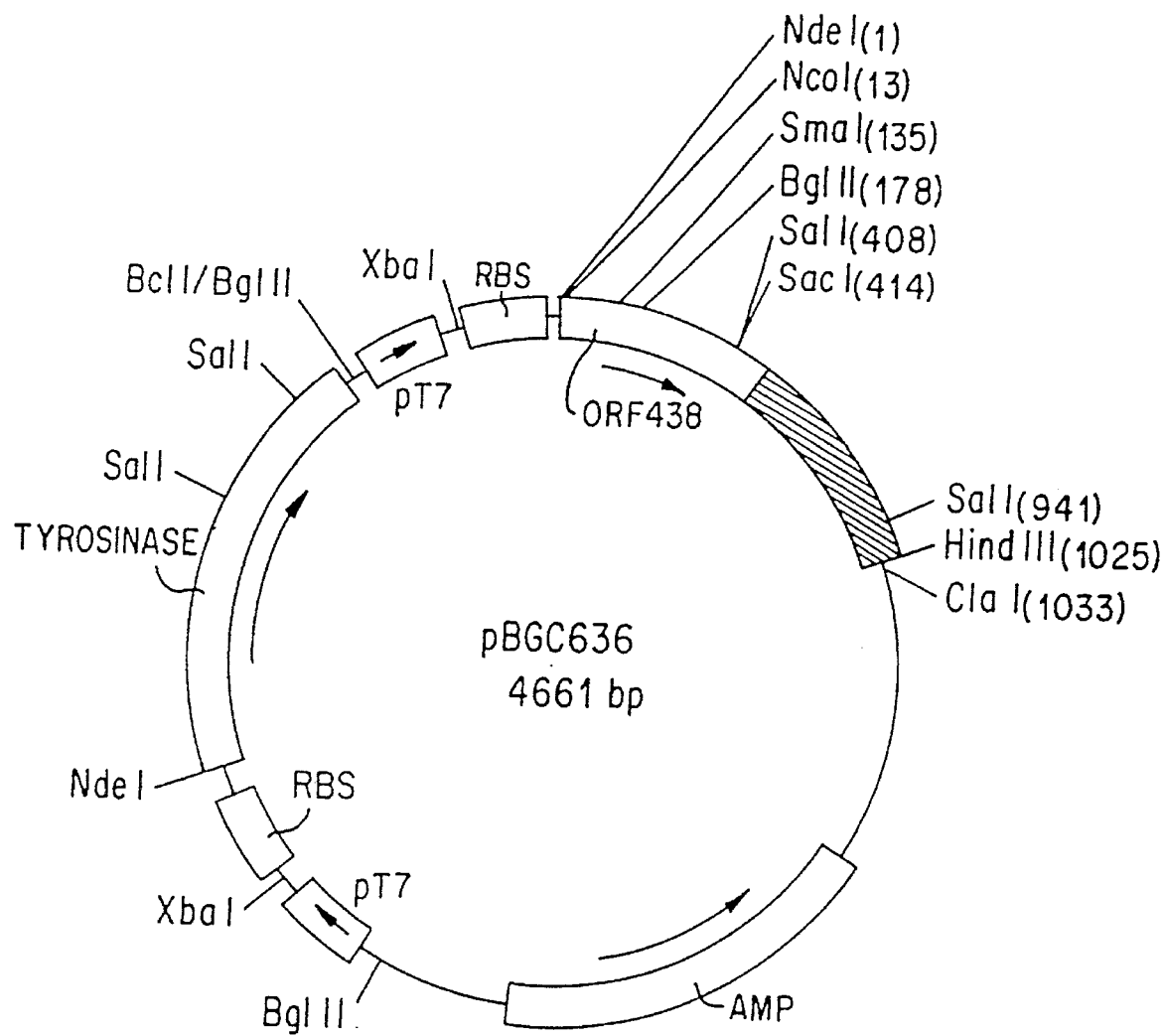
FIG. 4 provides the plasmid map of pBGC636.

Plasmid pBGC623 is a plasmid containing the nucleic acid sequence for ORF438. FIG. 2 provides the plasmid map of pBGC623. Plasmid pBGC635 is a plasmid containing a nucleic acid sequence for tyrosinase. FIG. 3 provides the plasmid map of pBGC635. Plasmid pBGC636 is a plasmid encoding for both ORF438 and tyrosinase under separate promoters. FIG. 4 provides the plasmid map of pBGC636. Preparation of plasmids pBGC623, pBGC635 and pBGC636 are taught in U.S. application Ser. No. 7/857,602 which is incorporated herein by reference.

2. Preparation of pBGC646

Figure 5:
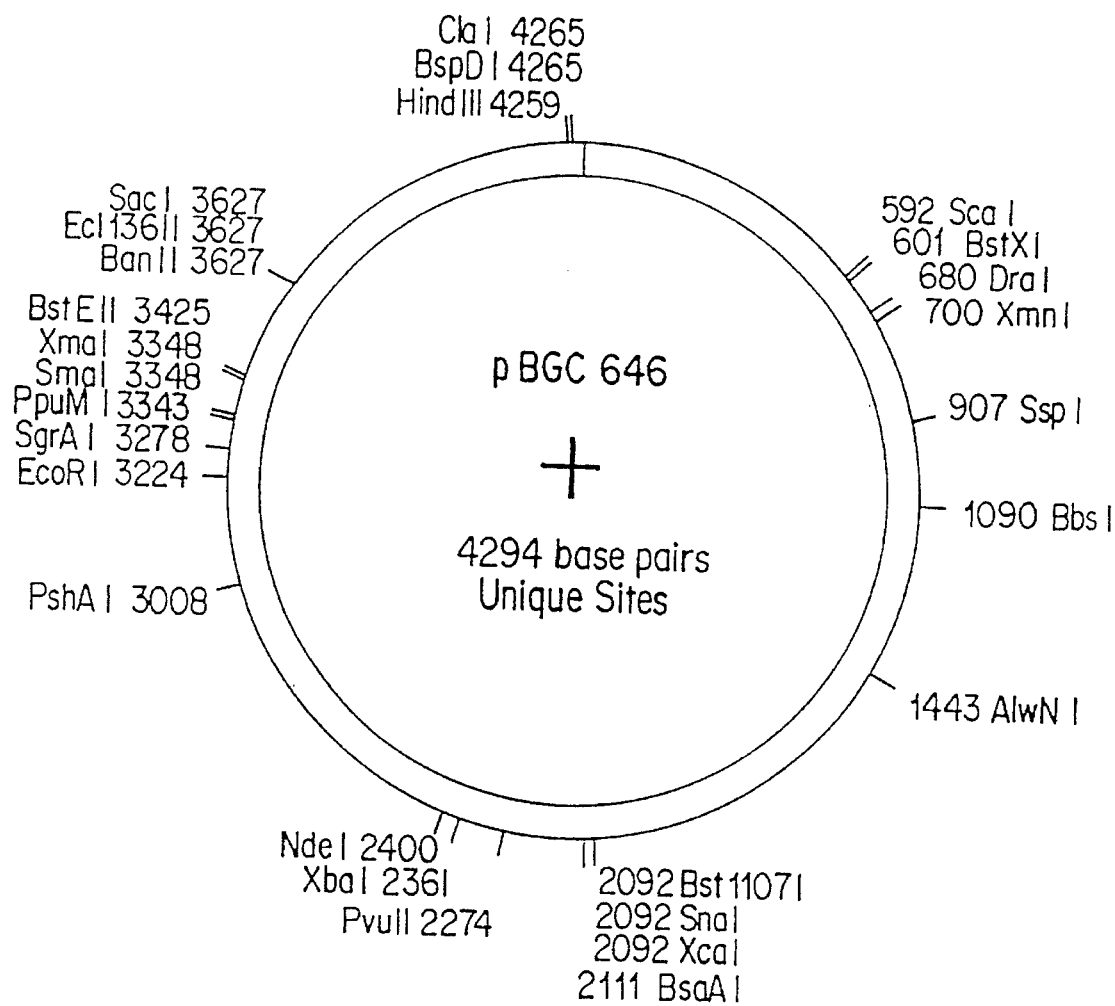
FIG. 5 provides the plasmid map of pBGC646.

In order to prepare pBGC646, the Bcl I site at the stop codon of the tyrosinase gene (in pBGC188Nde) was blunted with mung bean nuclease and ligated with a synthetic Eco RI linker (dGGAATTCC; SEQ. NO. 1). The tyrosinase gene was removed from plasmid pBGC188Nde as a 822bp Nde I/Eco RI fragment and gel purified in low melt agarose. The purified fragment was ligated into an ORF438 containing plasmid (pBGC623) that was modified as follows. Plasmid pBGC623 was cleaved with Nco I, blunted with mung bean nuclease, and ligated with a synthetic Eco RI linker (dGGAATTCC). The plasmid was gel purified in low melt agarose and ligated with the Nde I/Eco RI fragment containing the modified tyrosinase gene. FIG. 5 provides the plasmid map of pBGC646 [SEQ. NO. 2]. The translated amino acid sequence for the fusion enzyme encoded for by plasmid pBGC646 is provided as SEQ. NO. 3.

Transformants were screened in HB101 and two independent transformants were identified as having the correct orientation. These plasmids are pBS646.9 and pBS646.19, and both are identical. Both plasmids were transformed into *E. coli* strain K38 that harbors plasmid pGP1-2 and plated on agar containing tyrosine and copper. Both transformants gave a melanin phenotype as described previously (della, Cioppa, et al. *Bio/Technology* 8:634–638 (1990)), and were shown by SDS-PAGE to give a ~45kD band by SDS-PAGE. The hybrid tyrosinase/ORF438 fusion enzyme is predicted to encode a 45,806 MW protein with four additional amino acids linking the two functional domains (NH2-tyrosinase-trp-asn-ser-ala-ORF438-COOH).

3. Preparation of pBGC648

Figure 6:
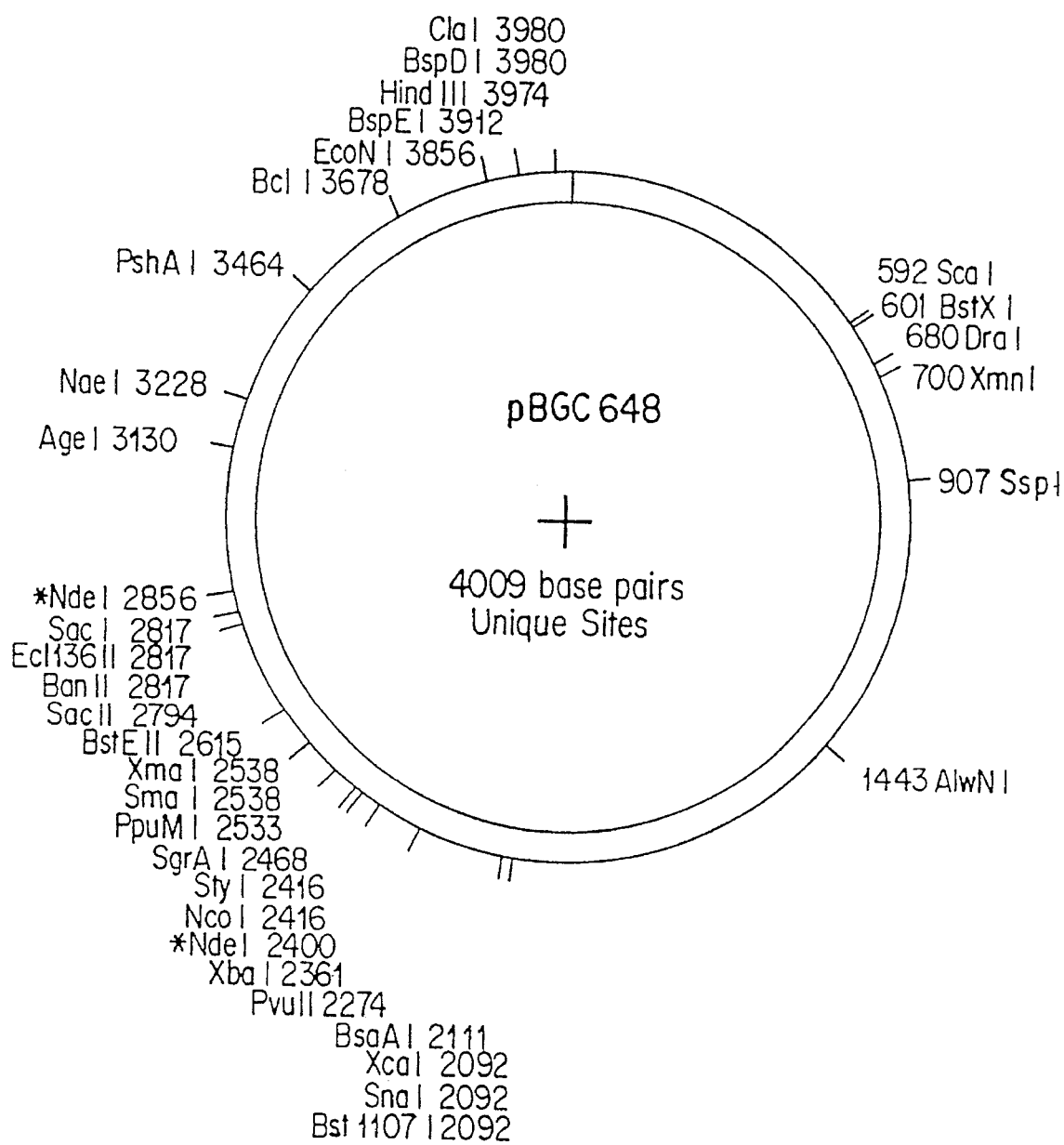
FIG. 6 provides the plasmid map of pBGC648.

To construct a second hybrid fusion gene between ORF438 and tyrosinase, the two synthetic oligonucleotides shown below 5'-dCCAGGGCGCCCGGCTCCTCCCCT-TCCCCTCCAACCA-3'[SEQ. NO. 4]3'-dTCGAGGTC-CCGCGGGCCGAGGAGGGGAAGGGGAGGTTGGTAT-5'[SEQ. NO. 5]were annealed, kinased, and used to clone into the Sac I site of the ORF438 gene. This replacement oligonucleotide sequence results in the destruction of the TGA stop codon of ORF438 and creates an in-frame NdeI site in its place for insertion of tyrosinase. A triple ligation reaction was set up that included the annealed oligonucleotide shown above, a 2,934 bp Hind III/Sac I fragment form pBGC623, and a 1,107 bp NdeI/Hind III fragment from pBGC635. The new plasmid (pBGC648) creates an ORF438/tyrosinase in-frame gene fusion that encodes a single polypeptide chain of 46,230 Daltons. The introduction of the new NdeI site introduces a single histidine residue between the two coding sequences upon translation. FIG. 6 provides the plasmid map of pBGC648. The nucleic acid sequence for pBGC648 is provided as SEQ. NO. 6. The translated amino acid sequence for the fusion enzyme encoded for by plasmid pBGC648 is provided as SEQ. NO. 7.

The DNA at the junction of the ORF438 and tyrosinase genes in plasmid pBGC648 were sequenced. Approximately 180 bp 3' of the Sac I site in the fusion were found to be correct, and the translated amino acid sequence is as predicted (See SEQ. No. 7). Plasmid pBGC648 was transformed into *E. coli* strain K38 that harbors plasmid pGP1-2 and plated on agar containing tyrosine and copper. The transformants gave a black melanin phenotype as described previously (della-Cioppa, et al., *Bio/Technology* 8:634–638 (1990)), and were shown by SDS-PAGE to give a ~46 kD band by SDS-PAGE. Transformants harboring pBGC648 give rise to the black melanin phenotype as rapidly as that seen when ORF438 and tyrosinase are expressed as single polypeptide chains from single genes. Phenotypically, the ORF438/tyrosinase gene fusion retains full catalytic activity similar to the wild type ~30 kD tyrosinase holoenzyme.

4. Transformation of *E. coli* with pBGC623, pBGC635, pBGC636, pBGC646 and pBGC648

Plasmids pBGC623, pBGC635, pBGC636, pBGC646 and pBGC648 were introduced into *E. coli* by pretreating exponentially growing cultures of the *E. coli* with $CaCl_2$ as described in Maniatis, et al., *Molecular Cloning* (1982).

5. Comparison Of Melanin Production By *E. coli* transformed with pBGC623, pBGC635, pBGC636, pBGC646 and pBGC648

Figure 7:
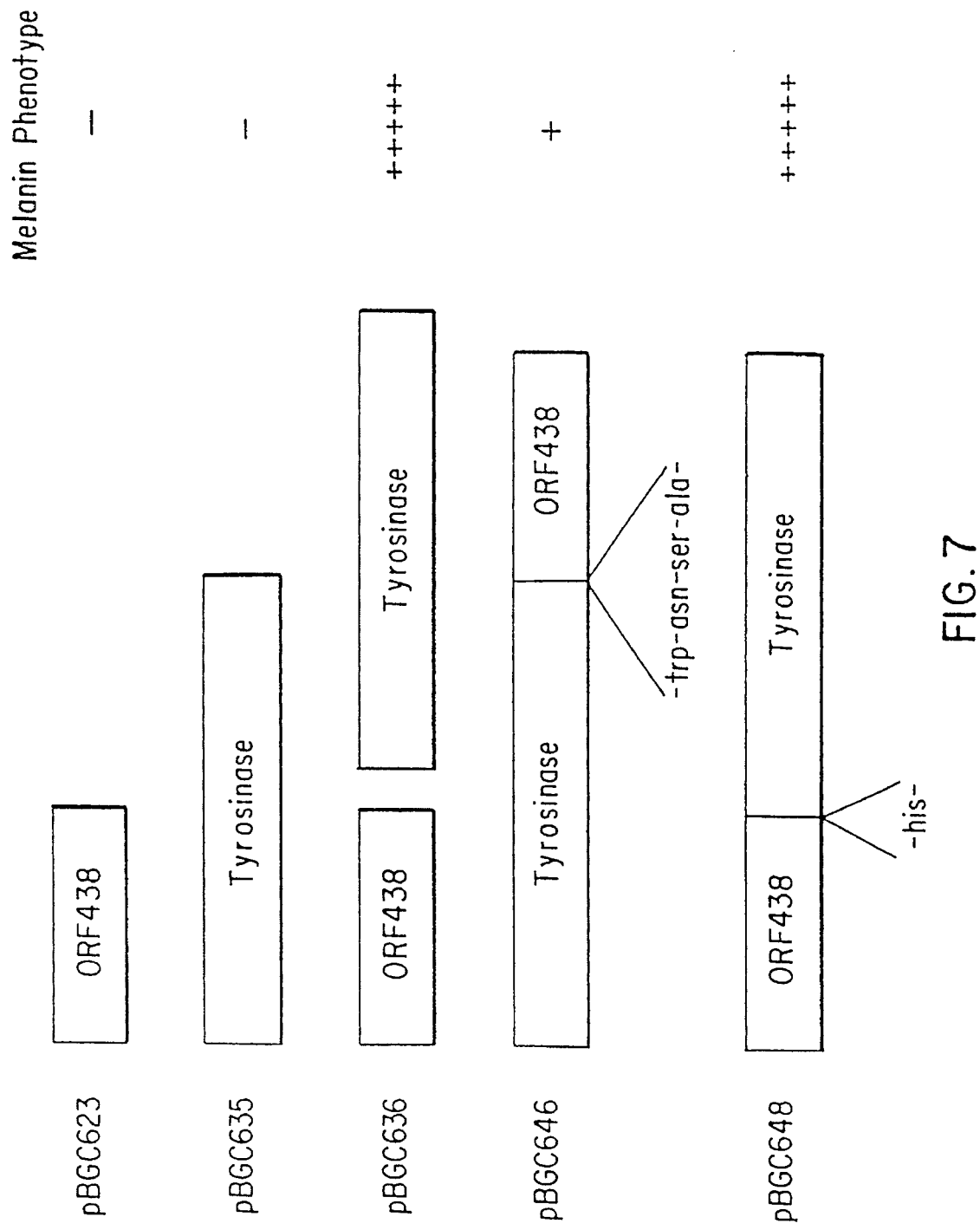
FIG. 7 provides a comparison of the melanin production capabilities of E. coli when transformed by plasmids pBGC623, pBGC635, pBGC636, pBGC646 and pBGC648.

Plasmids pBGC623, pBGC635, pBGC636, pBGC646 and pBGC648 were each introduced into *E. coli*. The transformed strains of *E. coli* were then grown on agar plates containing tyrosine and copper as described previously in della-Cioppa, et al., *Bio/Technology* 8 634 (1990) in order to evaluate each strains ability to produce melanin. FIG. 7 provides a comparison of the melanin production capabilities of *E. Coli* when transformed by these five different plasmids.

The amount of melanin formed was determined by the size and color intensities of black melanin halos that formed around the transformed *E. Coli* colonies. The rate of color development on agar plates, and the intensity of the black halo formation, is directly proportional to the level of tyrosinase enzymatic activity in each of the different plasnid bearing *E. coli* colonies. Melanin formation was quantitated as (−) none, (+) very weak, (++) weak, (+++) moderate, (++++) strong and (+++++) very strong.

*E. coli* transformed with either pBGC623 or pBGC635 do not produce a positive black melanin phenotype. *E. coli* transformed with pBGC636 produced a positive black melanin phenotype.

*E. coli* transformed with pBGC646 gave rise to a positive black melanin phenotype. However, *E. coli* transformed with pBGC646 produced melanin at a slower rate than *E. coli* transformed with pBGC636 in which ORF438 and tyrosinase are expressed as single polypeptide chains from single genes.

*E. coli* transformed with pBGC648 produced a positive black melanin phenotype at a comparable rate as pBGC636, indicating that the fusion enzyme produced by pBGC648 functions equally well as when ORF438 and tyrosinase are expressed independently.

6. Expression Of Tyrosinase/ORF438 Fusion Enzyme Containing Chloroplast Targeting Sequence In Plants For expression of a tyrosinase—activator protein fusion enzyme in higher plants, it may be advantageous to target the fusion enzyme to the chloroplast. Chloroplasts are known to contain the enzymatic pathway for production of L-tyrosine (the primary substrate for tyrosinase), and the oxidative environment inside the chloroplast may be well suited for achieving optimal enzymatic activity.

In order to target a tyrosinase—activator protein fusion enzyme to chloroplasts, the nucleotide sequence encoding the chloroplast transit peptide (CPT) from ribulose bisphosphate carboxylase small subunit (RuBPCase SSU) from *Nicotiana tabacum* was cloned (as an Nco I/Sph I fragment) and fused by way of its naturally occurring Sph I site (at the cysmet cleavage site of the CTP) to the naturally occurring Sph I site at the N-terminus of ORF438. The CTP/ORF438 nucleotide fusion was then exchanged as an Nco I/Sac I fragment in the plasmid BlueScript™ that contained the ORF438/tyrosinase sequence as described in plasmid pBS648. The resulting nucleotide sequence and translated amino acid sequence of the CTP/ORF438/tyrosinase fusion are shown in SEQ. No. 8 and SEQ. No. 9 respectively. The CTP/ORF438 tyrosinase fusion gene encodes 478 amino acids residues of which the 57 at the N-terminus direct the ORF438/tyrosinase fusion into the chloroplast. Upon import into the chloroplast compartment, the 57 amino acid CTP is proteolytically removed thus resulting in the identical ORF438/tyrosinase fusion enzyme of ~45 kD as previously produced in *E. Coli*. The CTP/ORF438/tyrosinase fusion enzyme has a deduced molecular weight of 51,461 Daltons.

The CTP/ORF438/tyrosinase nucleotide sequence may then be inserted into a viral construct such as those described in U.S. application Ser. No. 923,692, filed Jul. 31, 1992, or U.S. application Ser. No. 997,733, filed Dec. 30, 1992 and used to systemically infect higher plants.

While the invention has been disclosed by reference to the details of preferred embodiments, the disclosure is intended in an illustrative rather than in a limiting sense, as it is contemplated that modifications will readily occur to those skilled in the art, within the spirit of the invention and the scope of the appended claims.

What is claimed is:

1. A nucleic acid sequence encoding a fusion enzyme comprising a nucleic acid sequence encoding for a tyrosinase and a nucleic acid sequence encoding for a tyrosinase activator protein.

2. A nucleic acid sequence encoding a fusion enzyme according to claim 1 wherein the tyrosinase is derived from a prokaryote.

3. A nucleic acid sequence encoding a fusion enzyme according to claim 2 wherein the tyrosinase is derived from Streptomyces.

4. A nucleic acid sequence encoding a fusion enzyme according to claim 1 wherein the activator protein is selected from the group consisting of ORF438 and URF402.

5. A nucleic acid sequence encoding a fusion enzyme according to claim 1 wherein the activator protein is ORF438 and the tyrosinase is derived from *Streptomyces antibioticus*.

6. A nucleic acid sequence encoding a fusion enzyme according to claim 1 wherein the activator protein sequence is positioned 5' relative to the tyrosinase sequence.

7. A nucleic acid sequence encoding a fusion enzyme according to claim 1 wherein the tyrosinase sequence is positioned 5' relative to the the activator protein sequence.

8. A nucleic acid sequence encoding a fusion enzyme according to claim 6 wherein the activator protein is selected from the group consisting of ORF438 and URF402.

9. A nucleic acid sequence encoding a fusion enzyme according to claim 6 wherein the tyrosinase is derived from a prokaryote.

10. A nucleic acid sequence encoding a fusion enzyme according to claim 9 wherein the tyrosinase is derived from Streptomyces.

11. A nucleic acid sequence encoding a fusion enzyme according to claim 1 which further comprises a linker sequence positioned between the nucleic acid sequences encoding the activator protein and the tyrosinase.

12. A nucleic acid sequence encoding a fusion enzyme according to claim 11 wherein linker sequence encodes for a single amino acid.

13. A nucleic acid sequence encoding a fusion enzyme according to claim 12 wherein linker sequence encodes for a histidine residue.

14. A nucleic acid sequence encoding a fusion enzyme according to claim 11 wherein linker sequence encodes for a repeating Pro-Thr amino acid sequence.

15. A nucleic acid sequence encoding a fusion enzyme according to claim 11 wherein the nucleic acid sequence encoding the activator protein is positioned 5' relative to the nucleic acid sequence encoding the tyrosinase.

16. A nucleic acid sequence encoding a fusion enzyme according to claim 15 wherein the activator protein is selected from the group consisting of ORF438 and URF402.

17. A nucleic acid sequence encoding a fusion enzyme according to claim 15 wherein the tyrosinase is derived from a prokaryote.

18. A nucleic acid sequence encoding a fusion enzyme according to claim 17 wherein the tyrosinase is derived from Streptomyces.

19. A vector for transforming a prokaryotic organism, said vector comprising:
 a nucleic acid sequence encoding for a fusion enzyme, said fusion enzyme comprising an amino acid sequence for a tyrosinase and an amino acid sequence encoding for a tyrosinase activator protein; and
 a promoter sequence that regulates the transcription of the fusion enzyme.

20. A vector according to claim 19 wherein the activator protein sequence is positioned 5' relative to the tyrosinase sequence.

21. A vector according to claim 19 wherein the tyrosinase sequence is positioned 5' relative to the the activator protein sequence.

22. A vector according to claim 19 wherein the activator protein is selected from the group consisting of ORF438 and URF402.

23. A vector according to claim 19 wherein the tyrosinase is derived from a prokaryote.

24. A vector according to claim 23 wherein the tyrosinase is derived from Streptomyces.

25. A vector according to claim 19 wherein the activator protein is ORF438 and the tyrosinase is derived from *Streptomyces antibioticus*.

26. A vector according to claim 19 which further comprises a linker sequence positioned between the nucleic acid sequences encoding the activator protein and the tyrosinase.

27. A vector according to claim 26 wherein linker sequence encodes for a single amino acid.

28. A vector according to claim 27 wherein linker sequence encodes for a histidine residue.

29. A vector according to claim 26 wherein linker sequence encodes for a repeating Pro-Thr amino acid sequence.

30. A vector according to claim 19 wherein the activator protein is selected from the group consisting of ORF438 and URF402.

31. A vector according to claim 19 wherein the tyrosinase is derived from Streptomyces.

32. A fusion enzyme comprising an amino acid sequence for tyrosinase and an amino acid sequence for a tyrosinase activator protein.

33. A fusion enzyme according to claim 32 wherein the activator protein is selected from the group consisting of ORF438 and URF402.

34. A fusion enzyme according to claim 32 wherein the tyrosinase is derived from a prokaryote.

35. A fusion enzyme according to claim 34 wherein the tyrosinase is derived from Streptomyces.

36. A fusion enzyme according to claim 32 wherein the activator protein is ORF438 and the tyrosinase is derived from *Streptomyces antibioticus*.

37. A fusion enzyme according to claim 32 which further comprises a linker positioned between the amino acid sequences of the activator protein and the tyrosinase.

38. A fusion enzyme according to claim 37 wherein the linker sequence comprises a single amino acid.

39. A fusion enzyme according to claim 38 wherein the linker sequence comprises a histidine residue.

40. A fusion enzyme according to claim 37 wherein the linker sequence comprises a repeating Pro-Thr amino acid sequence.

41. A fusion enzyme according to claim 32 wherein the activator protein sequence is positioned on the N-terminus end of the tyrosinase sequence.

42. A fusion enzyme according to claim 41 wherein the activator protein is selected from the group consisting of ORF438 and URF402.

43. A fusion enzyme according to claim 41 wherein the tyrosinase is derived from a prokaryote.

44. A fusion enzyme according to claim 43 wherein the tyrosinase is derived from Streptomyces.

45. A fusion enzyme according to claim 34 wherein the activator protein sequence is positioned on the C-terminus end of the tyrosinase sequence.

46. A fusion enzyme according to claim 42 wherein the activator protein is selected from the group consisting of ORF438 and URF402.

47. A fusion enzyme according to claim 42 wherein the tyrosinase is derived from a prokaryote.

48. A fusion enzyme according to claim 47 wherein the tyrosinase is derived from Streptomyces.

49. A prokaryotic organism which has been transformed with a vector comprising a nucleic acid sequence encoding for a fusion enzyme said fusion enzyme comprising an amino acid sequence for a tyrosinase and an amino acid sequence encoding for a tyrosinase activator protein; and a promoter sequence that regulates the transcription of fusion enzyme.

50. A method of producing melanins, comprising the steps of:

(a) growing a prokaryotic organism which has been transformed with a vector comprising:

a nucleic acid sequence encoding for a fusion enzyme, said fusion enzyme comprising an amino acid sequence for a tyrosinase and an amino acid sequence encoding for a tyrosinase activator protein; and a promoter sequence that regulates the transcription of the fusion enzyme; and (b) isolating the melanin produced.

51. The method of claim 50 wherein said prokaryotic organism is selected from the group consisting of *Escherichia coli* and Streptomyces.

52. A nucleic acid sequence encoding a fusion enzyme comprising:

a nucleic acid sequence encoding for a protein that has cresolase activity and catecholase activity; and a nucleic acid encoding for a gene product that functions as a tyrosinase activator protein.

53. The nucleic acid sequence encoding a fusion enzyme of claim 52 further comprising a linker sequence positioned between said nucleic acid sequence encoding a gene product and said nucleotide sequence encoding a protein.

54. The nucleic acid sequence encoding a fusion enzyme of claim 53 wherein said linker sequence encodes for a His residue.

55. An amino acid sequence for a fusion enzyme comprising:

an amino acid sequence for a protein that has cresolase activity and catecholase activity; and an amino acid sequence for a protein that has a tyrosinase activator function.

56. The amino acid sequence of claim 55 further comprising a linker amino acid sequence positioned between said amino acid sequence with cresolase activity and catecholase activity and said amino acid sequence with a tyrosinase activating function.

57. The amino acid sequence encoding a fusion enzyme of claim 56 wherein said linker amino acid sequence comprises a His residue.

\* \* \* \* \*

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
      ( A ) LENGTH: 8
      ( B ) TYPE: nucleic acid
      ( C ) STRANDEDNESS: single
      ( D ) TOPOLOGY: linear ( i i ) MOLECULE TYPE:
      ( A ) DESCRIPTION: DNA ( i i i ) HYPOTHETICAL: NO ( i v ) ANTI-SENSE: NO ( v i ) ORIGINAL SOURCE:
      ( A ) ORGANISM:

( v i i ) IMMEDIATE SOURCE:
      ( B ) CLONE:

( i x ) FEATURE:

( x i ) SEQUENCE DESCRIPTION: SEQ ID NO: 1:

G G A A T T C C        8

( 2 ) INFORMATION FOR SEQ ID NO: 2:

( i ) SEQUENCE CHARACTERISTICS:
        ( A ) LENGTH: 4294
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA ( i i i ) HYPOTHETICAL: NO ( i v ) ANTI-SENSE: NO ( v i ) ORIGINAL SOURCE:
        ( A ) ORGANISM:

( v i i ) IMMEDIATE SOURCE:
        ( B ) CLONE:

( i x ) FEATURE:

( x i ) SEQUENCE DESCRIPTION: SEQ ID NO: 2:

| | | | | | |
|---|---|---|---|---|---|
| AAATCAATCT | AAAGTATATA | TGAGTAAACT | TGGTCTGACA | GTTACCAATG | CTTAATCAGT | 60 |
| GAGGCACCTA | TCTCAGCGAT | CTGTCTATTT | CGTTCATCCA | TAGTTGCCTG | ACTCCCCGTC | 120 |
| GTGTAGATAA | CTACGATACG | GGAGGGCTTA | CCATCTGGCC | CAGTGCTGCA | ATGATACCGC | 180 |
| GAGACCCACG | CTGACCGGCT | CCAGATTTAT | CAGCAATAAA | CCAGCCAGCC | GGAAGGGCCG | 240 |
| AGCGCAGAAG | TGGTCCTGCA | ACTTTATCCG | CCTCCATCCA | GTCTATTAAT | TGTTGCCGGG | 300 |
| AAGCTAGAGT | AAGTAGTTCG | CCAGTTAATA | GTTTGCGCAA | CGTTGTTGCC | ATTGCTACAG | 360 |
| GCATCGTGGT | GTCACGCTCG | GCGTTTGGTA | TGGCTTCATT | CAGCTCCGGT | TCCCAACGAT | 420 |
| CAAGGCGAGT | TACATGATCC | CCCATGTTGT | GCAAAAAAGC | GGTTAGCTCC | TTCGGTCCTC | 480 |
| CGATCGTTGT | CAGAAGTAAG | TTGGCCGCAG | TGTTATCACT | CATGGTTATG | GCAGCACTGC | 540 |
| ATAATTCTCT | TACTGTCATG | CCATCCGTAA | GATGCTTTTC | TGTGACTGGT | GAGTACTCAA | 600 |
| CCAAGTATTT | GGAAGATGCG | CGACCGAGTT | GCTCTTGCCC | GGCGTCAACA | CGGGATAATA | 660 |
| CCGCGCCACA | TAGCAGAACT | TTAAAAGTGC | TCATCATTGG | AAAACGTTCT | TCGGGGCGAA | 720 |
| AACTCTCAAG | GATCTTACCG | CTGTTGAGAT | CCAGTTCGAT | GTAACCCACT | CGTGCACCCA | 780 |
| ACTGATCTTC | AGCATCTTTT | ACTTTCACCA | GCGTTTCTGG | GTGAGCAAAA | ACAGGAAGGC | 840 |
| AAAATGCCGC | AAAAAAGGGA | ATAAGGGCGA | CACGGAAATG | TTGAATACTC | ATACTCTTCC | 900 |
| TTTTTCAATA | TTATTGAAGC | ATTTATCAGG | GTTATTGTCT | CATGAGCGGA | TACATATTTG | 960 |
| AATGTATTTA | GAAAAATAAA | CAAATAGGGG | TTCCGCGCAC | ATTTCCCCGA | AAAGTGCCAC | 1020 |
| CTGACGTCTA | AGAAACCATT | ATTATCATGA | CATTAACCTA | TAAAAATAGG | CGTATCACGA | 1080 |
| GGCCCTTTCG | TCTTCAAGAA | ttaaaaggat | ctaggtgaag | atcctttttg | ataatctcat | 1140 |
| gaccaaaatc | ccttaacgtg | agttttcgtt | ccactgagcg | tcagaccccg | tagaaaagat | 1200 |
| caaaggatct | tcttgagatc | ctttttttct | gcgcgtaatc | tgctgcttgc | aaacaaaaaa | 1260 |
| accaccgcta | ccagcggtgg | tttgtttgcc | ggatcaagag | ctaccaactc | tttttccgaa | 1320 |
| ggtaactggc | ttcagcagag | cgcagatacc | aaatactgtc | cttctagtgt | agccgtagtt | 1380 |
| aggccaccac | ttcaagaact | ctgtagcacc | gcctacatac | ctcgctctgc | taatcctgtt | 1440 |
| accagtggct | gctgccagtg | gcgataagtc | gtgtcttacc | gggttggact | caagacgata | 1500 |
| gttaccggat | aaggcgcagc | ggtcgggctg | aacggggggt | tcgtgcacac | agcccagctt | 1560 |
| ggagcgaacg | acctacaccg | aactgagata | cctacagcgt | gagctatgag | aaagcgccac | 1620 |

```
gcttcccgaa gggagaaagg cggacaggta tccggtaagc ggcagggtcg gaacaggaga   1680
gcgcacgagg gagcttccag ggggaaacgc ctggtatctt tatagtcctg tcgggtttcg   1740
ccacctctga cttgagcgtc gatttttgtg atgctcgtca gggggcgga gcctatggaa    1800
aaacgccagc aacgcggcct tttacggtt cctggccttt tgctggcctt ttgctcacat    1860
gttctttcct gcgttatccc ctgattcgt ggataaccgt attaccgcct ttgagtgagc    1920
tgataccgct cgccgcagcc gaacgaccga gcgcagcgag tcagtgagcg aggaagcgga   1980
agagcgcctg atgcggtatt ttctccttac gcatctgtgc ggtatttcac accgcaCAGA   2040
TCTGtggtgc actctcagta caatctgctc tgatgccgca tagttaagcc agtatacact   2100
ccgctatcgc tacgtgactg ggtcatggct gcgccccgac acccgccaac acccgctgac   2160
gcgccctgac gggcttgtct gctcccggca tccgcttaca gacaagctgt gaccgtctcc   2220
gggagctgca tgtgtcagag gttttcaccg tcatcaccga aacgcgcgag gCCcagctgC   2280
GATTCGAAct tctcgattcg aacttctgat agacttcgaa attaatacga ctcactatag   2340
ggagaccaca acggtttccc tctagaaata attttgttta actttaagaa ggagatatac   2400
atatgACCGT CCGCAAGAAC CAGGCGTCCC TGACCGCCGA GGAGAAGCGC CGCTTCGTCG   2460
CCGCCCTGCT CGAACTCAAG CGCACCGGCC GCTACGACGC CTTCGTCACC ACGCACAACG   2520
CGTTCATCCT GGGCGACACC GACAACGGCG AGCGCACCGG CCACCGTTCG CCGTCCTTCC   2580
TGCCCTGGCA CCGCAGATTT CTGCTGGAGT TCGAGCGGGC GCTCCAGTCG GTGGACGCGT   2640
CGGTGGCGCT GCCGTACTGG GACTGGTCCG CCGACCGGTC CACCCGGTCC TCGCTGTGGG   2700
CGCCGGACTT CCTCGGCGGC ACCGGGCGCA GCGGGACGG CCAGGTGATG GACGGGCCGT    2760
TCGCCGCGTC GGCCGGCAAC TGGCCGATCA ATGTGCGGGT GGACGGCCGT ACGTTCCTGC   2820
GGCGGGCGCT CGGCGCGGGC GTGAGCGAAC TGCCCACGCG TGCCGAGGTC GACTCGGTGC   2880
TGGCGATGGC GACGTACGAC ATGGCGCCCT GGAACAGCGG CTCCGACGGC TTCCGCAACC   2940
ATCTCGAAGG GTGGCGCGGG GTCAATCTGC ACAACCGGGT GCATGTCTGG GTCGGCGGCC   3000
AGATGGCGAC CGGGGTCTCC CCCAACGACC CGGTGTTCTG GCTGCACCAC GCCTACATCG   3060
ACAAGCTGTG GGCCGAGTGG CAGCGGCGGC ACCCCTCGTC CCCGTATCTG CCGGGCGGCG   3120
GCACGCCGAA CGTCGTCGAC CTCAACGAGA CGATGAAGCC GTGGAACGAC ACCACCCCGG   3180
CGGCCCTGCT GGACCACACC CGGCACTACA CCTTCGACGT Ctggaattcc GCGGAACTCA   3240
CCCGTCGTCG CGCGCTCGGC GCCGCAGCCG TCGTCGCCGC CGGTGTCCCG CTGGTCGCCC   3300
TTCCCGCCGC CCGCGCGGAC GATCGGGGGC ACCACACCCC CGAGGTCCCC GGGAACCCGG   3360
CCGCGTCCGG CGCCCCCGCC GCCTTCGACG AGATCTACAA GGGCCGCCGG ATACAGGGCC   3420
GGACGGTCAC CGACGGCGGG GGCCACCACG GCGGCGGTCA GGCGGTGAC GGTCACGGCG     3480
GCGGCCATCA CGGCGGCGGT TACGCCGTGT TCGTGGACGG CGTCGAACTG CATGTGATGC   3540
GCAACGCCGA CGGCTCGTGG ATCAGCGTCG TCAGCCACTA CGAGCCGGTG GACACCCCGC   3600
GCGCCGCGGC CCGCGCTGCG GTCGACGAGC TCCAGGGCGC CCGGCTCCTC CCCTTCCCCT   3660
CCAACtgaCC TTCTCCCCCG CACTTTTGGA GCACCGCAC atgACCGTCC GCAAGAACCA    3720
GGCGTCCCTG ACCGCCGAGG AGAAGCGCCG CTTCGTCGCC GCCCTGCTCG AACTCAAGCG   3780
CACCGGCCGC TACGACGCCT TCGTCACCAC GCACAACGCG TTCATCCTGG CGACACCGA    3840
CAACGGCGAG CGCACCGGCC ACCGTTCGCC GTCCTTCCTG CCCTGGCACC GCAGATTTCT   3900
GCTGGAGTTC GAGCGGGCGC TCCAGTCGGT GGACGCGTCG GTGGCGCTGC CGTACTGGGA   3960
CTGGTCCGCC GACCGGTCCA CCCGGTCCTC GCTGTGGGCG CCGGACTTCC TCGGCGGCAC   4020
```

```
CGGGCGCAGC  CGGGACGGCC  AGGTGATGGA  CGGGCCGTTC  GCCGCGTCGG  CCGGCAACTG       4080

GCCGATCAAT  GTGCGGGTGG  ACGGCCGTAC  GTTCCTGCGG  CGGGCGCTCG  GCGCGGGCGT       4140

GAGCGAACTG  CCCACGCGTG  CCGAGgtcga  cCTCAACGAG  ACGATGAAGC  CGTGGAACGA       4200

CACCACCCCG  GCGGCCCTGC  TGGACCACAC  CCGGCACTAC  ACCTTCGACG  TCtgaTCcaa       4260
gcttATCGAT  GATAAGCTGT  CAAACATGAG  AATT                                    4294
```

( 2 ) INFORMATION FOR SEQ ID NO: 3:

( i ) SEQUENCE CHARACTERISTICS:
        ( A ) LENGTH: 422
        ( B ) TYPE: amino acid
        ( C ) STRANDEDNESS:
        ( D ) TOPOLOGY: linear ( i i ) MOLECULE TYPE:
        ( A ) DESCRIPTION: protein ( i i i ) HYPOTHETICAL: NO ( i v ) ANTI-SENSE: NO ( v i ) ORIGINAL SOURCE:
        ( A ) ORGANISM:

( v i i ) IMMEDIATE SOURCE:
        ( B ) CLONE:

( i x ) FEATURE:

( x i ) SEQUENCE DESCRIPTION: SEQ ID NO: 3:

```
Met  Thr  Val  Arg  Lys  Asn  Gln  Ala  Ser  Leu  Thr  Ala  Glu  Glu  Lys
               5                        10                            15

Arg  Arg  Phe  Val  Ala  Leu  Leu  Glu  Leu  Lys  Arg  Thr  Gly  Arg
               20                       25                       30

Tyr  Asp  Ala  Phe  Val  Thr  Thr  His  Asn  Ala  Phe  Ile  Leu  Gly  Asp
                    35                       40                       45

Thr  Asp  Asn  Gly  Glu  Arg  Thr  Gly  His  Arg  Ser  Pro  Ser  Phe  Leu
                    50                       55                       60

Pro  Trp  His  Arg  Arg  Phe  Leu  Leu  Glu  Phe  Glu  Arg  Ala  Leu  Gln
                    65                       70                       75

Ser  Val  Asp  Ala  Ser  Val  Ala  Leu  Pro  Tyr  Trp  Asp  Trp  Ser  Ala
                    80                       85                       90

Asp  Arg  Ser  Thr  Arg  Ser  Ser  Leu  Trp  Ala  Pro  Asp  Phe  Leu  Gly
                    95                       100                      105

Gly  Thr  Gly  Arg  Ser  Arg  Asp  Gly  Gln  Val  Met  Asp  Gly  Pro  Phe
                    110                      115                      120

Ala  Ala  Ser  Ala  Gly  Asn  Trp  Pro  Ile  Asn  Val  Arg  Val  Asp  Gly
                    125                      130                      135

Arg  Thr  Phe  Leu  Arg  Arg  Ala  Leu  Gly  Ala  Gly  Val  Ser  Glu  Leu
                    140                      145                      150

Pro  Thr  Arg  Ala  Glu  Val  Asp  Ser  Val  Leu  Ala  Met  Ala  Thr  Tyr
                    155                      160                      165

Asp  Met  Ala  Pro  Trp  Asn  Ser  Gly  Ser  Asp  Gly  Phe  Arg  Asn  His
                    170                      175                      180

Leu  Glu  Gly  Trp  Arg  Gly  Val  Asn  Leu  His  Asn  Arg  Val  His  Val
                    185                      190                      195

Trp  Val  Gly  Gly  Gln  Met  Ala  Thr  Gly  Val  Ser  Pro  Asn  Asp  Pro
                    200                      205                      210

Val  Phe  Trp  Leu  His  His  Ala  Tyr  Ile  Asp  Lys  Leu  Trp  Ala  Glu
                    215                      220                      225
```

```
Trp  Gln  Arg  Arg  His  Pro  Ser  Ser  Pro  Tyr  Leu  Pro  Gly  Gly  Gly
                    230                      235                     240

Thr  Pro  Asn  Val  Val  Asp  Leu  Asn  Glu  Thr  Met  Lys  Pro  Trp  Asn
                    245                      250                     255

Asp  Thr  Thr  Pro  Ala  Ala  Leu  Leu  Asp  His  Thr  Arg  His  Tyr  Thr
                    260                      265                     270

Phe  Asp  Val  Trp  Asn  Ser  Ala  Glu  Leu  Thr  Arg  Arg  Arg  Ala  Leu
                    275                      280                     285

Gly  Ala  Ala  Ala  Val  Val  Ala  Ala  Gly  Val  Pro  Leu  Val  Ala  Leu
                    290                      295                     300

Pro  Ala  Ala  Arg  Ala  Asp  Asp  Arg  Gly  His  His  Thr  Pro  Glu  Val
                    305                      310                     315

Pro  Gly  Asn  Pro  Ala  Ala  Ser  Gly  Ala  Pro  Ala  Ala  Phe  Asp  Glu
                    320                      325                     330

Ile  Tyr  Lys  Gly  Arg  Arg  Ile  Gln  Gly  Arg  Thr  Val  Thr  Asp  Gly
                    335                      340                     345

Gly  Gly  His  His  Gly  Gly  Gly  His  Gly  Gly  Asp  Gly  His  Gly  Gly
                    350                      355                     360

Gly  His  His  Gly  Gly  Gly  Tyr  Ala  Val  Phe  Val  Asp  Gly  Val  Glu
                    365                      370                     375

Leu  His  Val  Met  Arg  Asn  Ala  Asp  Gly  Ser  Trp  Ile  Ser  Val  Val
                    380                      385                     390

Ser  His  Tyr  Glu  Pro  Val  Asp  Thr  Pro  Arg  Ala  Ala  Ala  Arg  Ala
                    395                      400                     405

Ala  Val  Asp  Glu  Leu  Gln  Gly  Ala  Arg  Leu  Leu  Pro  Phe  Pro  Ser
                    410                      415                     420

Asn  Gly
```

( 2 ) INFORMATION FOR SEQ ID NO: 4:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA ( i i i ) HYPOTHETICAL: NO ( i v ) ANTI-SENSE: NO ( v i ) ORIGINAL SOURCE:
        ( A ) ORGANISM:

( v i i ) IMMEDIATE SOURCE:
        ( B ) CLONE:

( i x ) FEATURE:

( x i ) SEQUENCE DESCRIPTION: SEQ ID NO: 4:

```
CCAGGGCGCC  CGGCTCCTCC  CCTTCCCCTC  CAACCA                              36
```

( 2 ) INFORMATION FOR SEQ ID NO: 5:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( i i ) MOLECULE TYPE:

(A) DESCRIPTION: DNA (iii) HYPOTHETICAL: NO (iv) ANTI-SENSE: NO (vi) ORIGINAL SOURCE:
    (A) ORGANISM:

(vii) IMMEDIATE SOURCE:
    (B) CLONE:

(ix) FEATURE:

(xi) SEQUENCE DESCRIPTION: SEQ ID NO: 5:

| | | | | | |
|---|---|---|---|---|---|
| TCGAGGTCCC | GCGGGCCGAG | GAGGGGAAGG | GGAGGTTGGT | AT | 42 |

(2) INFORMATION FOR SEQ ID NO: 6:

(i) SEQUENCE CHARACTERISTICS:
    (A) LENGTH: 4009
    (B) TYPE: nucleic acid
    (C) STRANDEDNESS: single
    (D) TOPOLOGY: circular (ii) MOLECULE TYPE:
    (A) DESCRIPTION: DNA (iii) HYPOTHETICAL: NO (iv) ANTI-SENSE: NO (vi) ORIGINAL SOURCE:
    (A) ORGANISM:

(vii) IMMEDIATE SOURCE:
    (B) CLONE:

(ix) FEATURE:

(xi) SEQUENCE DESCRIPTION: SEQ ID NO: 6:

| | | | | | |
|---|---|---|---|---|---|
| AAATCAATCT | AAAGTATATA | TGAGTAAACT | TGGTCTGACA | GTTACCAATG | CTTAATCAGT | 60 |
| GAGGCACCTA | TCTCAGCGAT | CTGTCTATTT | CGTTCATCCA | TAGTTGCCTG | ACTCCCCGTC | 120 |
| GTGTAGATAA | CTACGATACG | GGAGGGCTTA | CCATCTGGCC | CAGTGCTGCA | ATGATACCGC | 180 |
| GAGACCCACG | CTGACCGGCT | CCAGATTTAT | CAGCAATAAA | CCAGCCAGCC | GGAAGGGCCG | 240 |
| AGCGCAGAAG | TGGTCCTGCA | ACTTTATCCG | CCTCCATCCA | GTCTATTAAT | TGTTGCCGGG | 300 |
| AAGCTAGAGT | AAGTAGTTCG | CCAGTTAATA | GTTTGCGCAA | CGTTGTTGCC | ATTGCTACAG | 360 |
| GCATCGTGGT | GTCACGCTCG | GCGTTTGGTA | TGGCTTCATT | CAGCTCCGGT | TCCCAACGAT | 420 |
| CAAGGCGAGT | TACATGATCC | CCCATGTTGT | GCAAAAAAGC | GGTTAGCTCC | TTCGGTCCTC | 480 |
| CGATCGTTGT | CAGAAGTAAG | TTGGCCGCAG | TGTTATCACT | CATGGTTATG | GCAGCACTGC | 540 |
| ATAATTCTCT | TACTGTCATG | CCATCCGTAA | GATGCTTTTC | TGTGACTGGT | GAGTACTCAA | 600 |
| CCAAGTATTT | GGAAGATGCG | CGACCGAGTT | GCTCTTGCCC | GGCGTCAACA | CGGGATAATA | 660 |
| CCGCGCCACA | TAGCAGAACT | TTAAAAGTGC | TCATCATTGG | AAAACGTTCT | TCGGGGCGAA | 720 |
| AACTCTCAAG | GATCTTACCG | CTGTTGAGAT | CCAGTTCGAT | GTAACCCACT | CGTGCACCCA | 780 |
| ACTGATCTTC | AGCATCTTTT | ACTTTCACCA | GCGTTTCTGG | GTGAGCAAAA | ACAGGAAGGC | 840 |
| AAAATGCCGC | AAAAAAGGGA | ATAAGGGCGA | CACGGAAATG | TTGAATACTC | ATACTCTTCC | 900 |
| TTTTTCAATA | TTATTGAAGC | ATTTATCAGG | GTTATTGTCT | CATGAGCGGA | TACATATTTG | 960 |
| AATGTATTTA | GAAAAATAAA | CAAATAGGGG | TTCCGCGCAC | ATTTCCCCGA | AAAGTGCCAC | 1020 |
| CTGACGTCTA | AGAAACCATT | ATTATCATGA | CATTAACCTA | TAAAAATAGG | CGTATCACGA | 1080 |

| | | | | | |
|---|---|---|---|---|---|
| GGCCCTTTCG | TCTTCAAGAA | ttaaaaggat | ctaggtgaag | atcctttttg | ataatctcat | 1140 |
| gaccaaaatc | ccttaacgtg | agttttcgtt | ccactgagcg | tcagaccccg | tagaaaagat | 1200 |
| caaaggatct | tcttgagatc | ctttttttct | gcgcgtaatc | tgctgcttgc | aaacaaaaaa | 1260 |
| accaccgcta | ccagcggtgg | tttgtttgcc | ggatcaagag | ctaccaactc | tttttccgaa | 1320 |
| ggtaactggc | ttcagcagag | cgcagatacc | aaatactgtc | cttctagtgt | agccgtagtt | 1380 |
| aggccaccac | ttcaagaact | ctgtagcacc | gcctacatac | ctcgctctgc | taatcctgtt | 1440 |
| accagtggct | gctgccagtg | gcgataagtc | gtgtcttacc | gggttggact | caagacgata | 1500 |
| gttaccggat | aaggcgcagc | ggtcgggctg | aacggggggt | tcgtgcacac | agcccagctt | 1560 |
| ggagcgaacg | acctacaccg | aactgagata | cctacagcgt | gagctatgag | aaagcgccac | 1620 |
| gcttcccgaa | gggagaaagg | cggacaggta | tccggtaagc | ggcagggtcg | gaacaggaga | 1680 |
| gcgcacgagg | gagcttccag | ggggaaacgc | ctggtatctt | tatagtcctg | tcgggtttcg | 1740 |
| ccacctctga | cttgagcgtc | gatttttgtg | atgctcgtca | ggggggcgga | gcctatggaa | 1800 |
| aaacgccagc | aacgcggcct | ttttacggtt | cctggccttt | tgctggcctt | ttgctcacat | 1860 |
| gttctttcct | gcgttatccc | ctgattctgt | ggataaccgt | attaccgcct | ttgagtgagc | 1920 |
| tgataccgct | cgccgcagcc | gaacgaccga | gcgcagcgag | tcagtgagcg | aggaagcgga | 1980 |
| agagcgcctg | atgcggtatt | ttctccttac | gcatctgtgc | ggtatttcac | accgcaCAGA | 2040 |
| TCTGtggtgc | actctcagta | caatctgctc | tgatgccgca | tagttaagcc | agtatacact | 2100 |
| ccgctatcgc | tacgtgactg | ggtcatggct | gcgccccgac | acccgccaac | acccgctgac | 2160 |
| gcgccctgac | gggcttgtct | gctcccggca | tccgcttaca | gacaagctgt | gaccgtctcc | 2220 |
| gggagctgca | tgtgtcagag | gttttcaccg | tcatcaccga | aacgcgcgag | gCCcagctgC | 2280 |
| GATTCGAAct | tctcgattcg | aacttctgat | agacttcgaa | attaatacga | ctcactatag | 2340 |
| ggagaccaca | acggtttccc | TCTAGAaata | attttgttta | actttaagaa | ggagatatac | 2400 |
| atATGGCTAG | AATTGCCatg | GCGGAACTCA | CCCGTCGTCG | CGCGCTCGGC | GCCGCAGCCG | 2460 |
| TCGTCGCCGC | CGGTGTCCCG | CTGGTCGCCC | TTCCCGCCGC | CCGCGCGGAC | GATCGGGGGC | 2520 |
| ACCACACCCC | CGAGGTCCCC | GGGAACCCGG | CCGCGTCCGG | CGCCCCCGCC | GCCTTCGACG | 2580 |
| AGATCTACAA | GGGCCGCCGG | ATACAGGGCC | GGACGGTCAC | CGACGGCGGG | GGCCACCACG | 2640 |
| GCGGCGGTCA | CGGCGGTGAC | GGTCACGGCG | GCGGCCATCA | CGGCGGCGGT | TACGCCGTGT | 2700 |
| TCGTGGACGG | CGTCGAACTG | CATGTGATGC | GCAACGCCGA | CGGCTCGTGG | ATCAGCGTCG | 2760 |
| TCAGCCACTA | CGAGCCGGTG | GACACCCCGC | GCGCCGCGGC | CCGCGCTGCG | GTCGACGAGC | 2820 |
| TCCAGGGCGC | CCGGCTCCTC | CCCTTCCCCT | CCAACcatAT | GACCGTCCGC | AAGAACCAGG | 2880 |
| CGTCCCTGAC | CGCCGAGGAG | AAGCGCCGCT | TCGTCGCCGC | CCTGCTCGAA | CTCAAGCGCA | 2940 |
| CCGGCCGCTA | CGACGCCTTC | GTCACCACGC | ACAACGCGTT | CATCCTGGGC | GACACCGACA | 3000 |
| ACGGCGAGCG | CACCGGCCAC | CGTTCGCCGT | CCTTCCTGCC | CTGGCACCGC | AGATTTCTGC | 3060 |
| TGGAGTTCGA | GCGGGCGCTC | CAGTCGGTGG | ACGCGTCGGT | GGCGCTGCCG | TACTGGGACT | 3120 |
| GGTCCGCCGA | CCGGTCCACC | CGGTCCTCGC | TGTGGGCGCC | GGACTTCCTC | GGCGGCACCG | 3180 |
| GGCGCAGCCG | GGACGGCCAG | GTGATGGACG | GCCGTTCGC | CGCGTCGGCC | GGCAACTGGC | 3240 |
| CGATCAATGT | GCGGGTGGAC | GGCCGTACGT | TCCTGCGGCG | GGCGCTCGGC | GCGGGCGTGA | 3300 |
| GCGAACTGCC | CACGCGTGCC | GAGGTCGACT | CGGTGCTGGC | GATGGCGACG | TACGACATGG | 3360 |
| CGCCCTGGAA | CAGCGGCTCC | GACGGCTTCC | GCAACCATCT | CGAAGGGTGG | CGCGGGGTCA | 3420 |
| ATCTGCACAA | CCGGGTGCAT | GTCTGGGTCG | GCGGCCAGAT | GGCGACCGGG | GTCTCCCCCA | 3480 |

```
ACGACCCGGT  GTTCTGGCTG  CACCACGCCT  ACATCGACAA  GCTGTGGGCC  GAGTGGCAGC    3540

GGCGGCACCC  CTCGTCCCCG  TATCTGCCGG  GCGGCGGCAC  GCCGAACGTC  GTCGACCTCA    3600

ACGAGACGAT  GAAGCCGTGG  AACGACACCA  CCCCGGCGGC  CCTGCTGGAC  CACACCCGGC    3660

ACTACACCTT  CGACGTCtga  tcatcactga  cgaatcgagg  tcgaggaacc  gagcgtccga    3720
ggaacagagg  cgcttatcgg  ttggccgcga  gattcctgtc  gatcctctcg  tgcagcgcga    3780
ttccgaggga  aacggaaacg  ttgagagact  cggtctggct  catcatgggg  atggaaaccg    3840
aggcggaaga  cgcctcctcg  aacaggtcgg  aaggcccacc  ctttcgctg   ccgaacagca    3900 aggccagccg  atccggattg  tccccgagtt  ccttcacgga  aatgtcgcca  tccgccttga    3960
gcgtcatcag  ATCaagcttA  TCGATGATAA  GCTGTCAAAC  ATGAGAATT                 4009
```

( 2 ) INFORMATION FOR SEQ ID NO: 7:

( i ) SEQUENCE CHARACTERISTICS:
        ( A ) LENGTH: 426
        ( B ) TYPE: amino acid
        ( C ) STRANDEDNESS:
        ( D ) TOPOLOGY: circular ( i i ) MOLECULE TYPE:
        ( A ) DESCRIPTION: protein ( i i i ) HYPOTHETICAL: NO ( i v ) ANTI-SENSE: NO ( v i ) ORIGINAL SOURCE:
        ( A ) ORGANISM:

( v i i ) IMMEDIATE SOURCE:
        ( B ) CLONE:

( i x ) FEATURE:

( x i ) SEQUENCE DESCRIPTION: SEQ ID NO: 7:

```
MET  ALA  ARG  ILE  ALA  MET  ALA  GLU  LEU  THR  ARG  ARG  ARG  ALA  LEU
               5                        10                           15

GLY  ALA  ALA  ALA  VAL  VAL  ALA  ALA  GLY  VAL  PRO  LEU  VAL  ALA  LEU
              20                        25                           30

PRO  ALA  ALA  ARG  ALA  ASP  ASP  ARG  GLY  HIS  HIS  THR  PRO  GLU  VAL
              35                        40                           45

PRO  GLY  ASN  PRO  ALA  ALA  SER  GLY  ALA  PRO  ALA  ALA  PHE  ASP  GLU
              50                        55                           60

ILE  TYR  LYS  GLY  ARG  ARG  ILE  GLN  GLY  ARG  THR  VAL  THR  ASP  GLY
              65                        70                           75

GLY  GLY  HIS  HIS  GLY  GLY  GLY  HIS  GLY  GLY  ASP  GLY  HIS  GLY  GLY
              80                        85                           90

GLY  HIS  HIS  GLY  GLY  GLY  TYR  ALA  VAL  PHE  VAL  ASP  GLY  VAL  GLU
              95                       100                          105

LEU  HIS  VAL  MET  ARG  ASN  ALA  ASP  GLY  SER  TRP  ILE  SER  VAL  VAL
             110                       115                          120

SER  HIS  TYR  GLU  PRO  VAL  ASP  THR  PRO  ARG  ALA  ALA  ALA  ARG  ALA
             125                       130                          135

ALA  VAL  ASP  GLU  LEU  GLN  GLY  ALA  ARG  LEU  LEU  PRO  PHE  PRO  SER
             140                       145                          150

ASN  HIS  MET  THR  VAL  ARG  LYS  ASN  GLN  ALA  SER  LEU  THR  ALA  GLU
             155                       160                          165

GLU  LYS  ARG  ARG  PHE  VAL  ALA  ALA  LEU  LEU  GLU  LEU  LYS  ARG  THR
             170                       175                          180
```

| | | | | | | | | | | | | | | |
|---|---|---|---|---|---|---|---|---|---|---|---|---|---|---|
| GLY | ARG | TYR | ASP | ALA<br>185 | PHE | VAL | THR | THR | HIS<br>190 | ASN | ALA | PHE | ILE | LEU<br>195 |
| GLY | ASP | THR | ASP | ASN<br>200 | GLY | GLU | ARG | THR | GLY<br>205 | HIS | ARG | SER | PRO | SER<br>210 |
| PHE | LEU | PRO | TRP | HIS<br>215 | ARG | ARG | PHE | LEU | LEU<br>215 | GLU | PHE | GLU | ARG | ALA<br>220 |
| LEU | GLN | SER | VAL | ASP<br>225 | ALA | SER | VAL | ALA | LEU<br>230 | PRO | TYR | TRP | ASP | TRP<br>235 |
| SER | ALA | ASP | ARG | SER<br>240 | THR | ARG | SER | SER | LEU<br>245 | TRP | ALA | PRO | ASP | PHE<br>250 |
| LEU | GLY | GLY | THR | GLY<br>255 | ARG | SER | ARG | ASP | GLY<br>260 | GLN | VAL | MET | ASP | GLY<br>265 |
| PRO | PHE | ALA | ALA | SER<br>270 | ALA | GLY | ASN | TRP | PRO<br>275 | ILE | ASN | VAL | ARG | VAL<br>280 |
| ASP | GLY | ARG | THR | PHE<br>285 | LEU | ARG | ARG | ALA | LEU<br>290 | GLY | ALA | GLY | VAL | SER<br>295 |
| GLU | LEU | PRO | THR | ARG<br>300 | ALA | GLU | VAL | ASP | SER<br>305 | VAL | LEU | ALA | MET | ALA<br>310 |
| THR | TYR | ASP | MET | ALA<br>315 | PRO | TRP | ASN | SER | GLY<br>320 | SER | ASP | GLY | PHE | ARG<br>325 |
| ASN | HIS | LEU | GLU | GLY<br>330 | TRP | ARG | GLY | VAL | ASN<br>335 | LEU | HIS | ASN | ARG | VAL<br>340 |
| HIS | VAL | TRP | VAL | GLY<br>345 | GLY | GLN | MET | ALA | THR<br>350 | GLY | VAL | SER | PRO | ASN<br>355 |
| ASP | PRO | VAL | PHE | TRP<br>360 | LEU | HIS | HIS | ALA | TYR<br>370 | ILE | ASP | LYS | LEU | TRP<br>375 |
| ALA | GLU | TRP | GLN | ARG<br>380 | ARG | HIS | PRO | SER | SER<br>385 | PRO | TYR | LEU | PRO | GLY<br>390 |
| GLY | GLY | THR | PRO | ASN<br>395 | VAL | VAL | ASP | LEU | ASN<br>400 | GLU | THR | MET | LYS | PRO<br>405 |
| TRP | ASN | ASP | THR | THR<br>410 | PRO | ALA | ALA | LEU | LEU<br>415 | ASP | HIS | THR | ARG | HIS<br>420 |
| TYR | THR | PHE | ASP | VAL<br>425 | GLY | | | | | | | | | |

( 2 ) INFORMATION FOR SEQ ID NO: 8:

( i ) SEQUENCE CHARACTERISTICS:
        ( A ) LENGTH: 1442
        ( B ) TYPE: nucleic acid
        ( C ) STRANDEDNESS: single
        ( D ) TOPOLOGY: linear ( i i ) MOLECULE TYPE:
        ( A ) DESCRIPTION: DNA ( i i i ) HYPOTHETICAL: NO ( i v ) ANTI-SENSE: NO ( v i ) ORIGINAL SOURCE:
        ( A ) ORGANISM:

( v i i ) IMMEDIATE SOURCE:
        ( B ) CLONE:

( i x ) FEATURE:

( x i ) SEQUENCE DESCRIPTION: SEQ ID NO: 8:

```
ctcgagccAT GGCTTCCTCA GTTCTTTCCT CTGCAGCAGT TGCCACCCGC AGCAATGTTG      60
CTCAAGCTAA CATGGTTGCA CCTTTCACTG GCCTTAAGTC AGCTGCCTCA TTCCCTGTTT     120
```

| | | | | | | |
|---|---|---|---|---|---|---|
| CAAGGAAGCA | AAACCTTGAC | ATCACTTCCA | TTGCCAGCAA | CGGCGGAAGA | GTGCAATGCA | 180 |
| TGCCGGAACT | CACCCGTCGT | CGCGCGCTCG | GCGCCGCAGC | CGTCGTCGCC | GCCGGTGTCC | 240 |
| CGCTGGTCGC | CCTTCCCGCC | GCCCGCGCGG | ACGATCGGGG | GCACCACACC | CCCGAGGTCC | 300 |
| CCGGGAACCC | GGCCGCGTCC | GGCGCCCCCG | CCGCCTTCGA | CGAGATCTAC | AAGGGCCGCC | 360 |
| GGATACAGGG | CCGGACGGTC | ACCGACGGCG | GGGGCCACCA | CGGCGGCGGT | CACGGCGGTG | 420 |
| ACGGTCACGG | CGGCGGCCAT | CACGGCGGCG | GTTACGCCGT | GTTCGTGGAC | GGCGTCGAAC | 480 |
| TGCATGTGAT | GCGCAACGCC | GACGGCTCGT | GGATCAGCGT | CGTCAGCCAC | TACGAGCCGG | 540 |
| TGGACACCCC | GCGCGCCGCG | GCCCGCGCTG | CGGTCGACGA | GCTCCAGGGC | GCCCGGCTCC | 600 |
| TCCCCTTCCC | CTCCAACCAT | ATGACCGTCC | GCAAGAACCA | GGCGTCCCTG | ACCGCCGAGG | 660 |
| AGAAGCGCCG | CTTCGTCGCC | GCCCTGCTCG | AACTCAAGCG | CACCGGCCGC | TACGACGCCT | 720 |
| TCGTCACCAC | GCACAACGCG | TTCATCCTGG | GCGACACCGA | CAACGGCGAG | CGCACCGGCC | 780 |
| ACCGTTCGCC | GTCCTTCCTG | CCCTGGCACC | GCAGATTTCT | GCTGGAGTTC | GAGCGGGCGC | 840 |
| TCCAGTCGGT | GGACGCGTCG | GTGGCGCTGC | CGTACTGGGA | CTGGTCCGCC | GACCGGTCCA | 900 |
| CCCGGTCCTC | GCTGTGGGCG | CCGGACTTCC | TCGGCGGCAC | CGGGCGCAGC | CGGGACGGCC | 960 |
| AGGTGATGGA | CGGGCCGTTC | GCCGCGTCGG | CCGGCAACTG | GCCGATCAAT | GTGCGGGTGG | 1020 |
| ACGGCCGTAC | GTTCCTGCGG | CGGGCGCTCG | GCGCGGGCGT | GAGCGAACTG | CCCACGCGTG | 1080 |
| CCCAGGTCGA | CTCGGTGCTG | GCGATGGCGA | CGTACGACAT | GGCGCCCTGG | AACAGCGGCT | 1140 |
| CCGACGGCTT | CCGCAACCAT | CTCGAAGGGT | GGCGCGGGGT | CAATCTGCAC | AACCGGGTGC | 1200 |
| ATGTCTGGGT | CGGCGGCCAG | ATGGCGACCG | GGGTCTCCCC | CAACGACCCG | GTGTTCTGGC | 1260 |
| TGCACCACGC | CTACATCGAC | AAGCTGTGGG | CCGAGTGGCA | GCGGCGGCAC | CCCTCGTCCC | 1320 |
| CGTATCTGCC | GGGCGGCGGC | ACGCCGAACG | TCGTCGACCT | CAACGAGACG | ATGAAGCCGT | 1380 |
| GGAACCACAC | CACCCCGGCG | GCCCTGCTGG | ACCACACCCG | GCACTACACC | TTCGACGTCT | 1440 |
| GA | | | | | | 1442 |

( 2 ) INFORMATION FOR SEQ ID NO: 9:

( i ) SEQUENCE CHARACTERISTICS:
( A ) LENGTH: 478
( B ) TYPE: amino acid
( C ) STRANDEDNESS: single
( D ) TOPOLOGY: linear ( i i ) MOLECULE TYPE:
( A ) DESCRIPTION: DNA ( i i i ) HYPOTHETICAL: NO ( i v ) ANTI-SENSE: NO ( v i ) ORIGINAL SOURCE:
( A ) ORGANISM:

( v i i ) IMMEDIATE SOURCE:
( B ) CLONE:

( i x ) FEATURE:

( x i ) SEQUENCE DESCRIPTION: SEQ ID NO: 9:

Met Ala Ser Ser Val Leu Ser Ser Ala Ala Val Ala Thr Arg Ser
                      5                           10                         15

Asn Val Ala Gln Ala Asn Met Val Ala Pro Phe Thr Gly Leu Lys
                    20                          25                         30

Ser Ala Ala Ser Phe Pro Val Ser Arg Lys Gln Asn Leu Asp Ile

-continued

|  |  |  | 35 |  |  |  |  | 40 |  |  |  | 45 |
|---|---|---|---|---|---|---|---|---|---|---|---|---|
| Thr | Ser | Ile | Ala | Ser | Asn | Gly | Gly | Arg | Val | Gln | Cys | Met | Pro | Glu |
|  |  |  | 50 |  |  |  |  | 55 |  |  |  | 60 |
| Leu | Thr | Arg | Arg | Arg | Ala | Leu | Gly | Ala | Ala | Ala | Val | Val | Ala | Ala |
|  |  |  | 65 |  |  |  |  | 70 |  |  |  | 75 |
| Gly | Val | Pro | Leu | Val | Ala | Leu | Pro | Ala | Ala | Arg | Ala | Asp | Asp | Arg |
|  |  |  | 80 |  |  |  |  | 85 |  |  |  | 90 |
| Gly | His | His | Thr | Pro | Glu | Val | Pro | Gly | Asn | Pro | Ala | Ala | Ser | Gly |
|  |  |  | 95 |  |  |  |  | 100 |  |  |  | 105 |
| Ala | Pro | Ala | Ala | Phe | Asp | Glu | Ile | Tyr | Lys | Gly | Arg | Arg | Ile | Gln |
|  |  |  | 110 |  |  |  |  | 115 |  |  |  | 120 |
| Gly | Arg | Thr | Val | Thr | Asp | Gly | Gly | Gly | Asp | His | Gly | Gly | Gly | His |
|  |  |  | 125 |  |  |  |  | 130 |  |  |  | 135 |
| Gly | Gly | Asp | Gly | His | Gly | Gly | Gly | His | His | Gly | Gly | Gly | Tyr | Ala |
|  |  |  | 140 |  |  |  |  | 145 |  |  |  | 150 |
| Val | Phe | Val | Asp | Gly | Val | Glu | Leu | His | Val | Met | Arg | Asn | Ala | Asp |
|  |  |  | 155 |  |  |  |  | 160 |  |  |  | 165 |
| Gly | Ser | Trp | Ile | Ser | Val | Val | Ser | His | Tyr | Glu | Pro | Val | Asp | Thr |
|  |  |  | 170 |  |  |  |  | 175 |  |  |  | 180 |
| Pro | Arg | Ala | Ala | Ala | Arg | Ala | Ala | Val | Asp | Glu | Leu | Gln | Gly | Ala |
|  |  |  | 185 |  |  |  |  | 190 |  |  |  | 195 |
| Arg | Leu | Leu | Pro | Phe | Pro | Ser | Asn | His | Met | Thr | Val | Arg | Lys | Asn |
|  |  |  | 200 |  |  |  |  | 205 |  |  |  | 210 |
| Gln | Ala | Ser | Leu | Thr | Ala | Glu | Glu | Lys | Arg | Arg | Phe | Val | Ala | Ala |
|  |  |  | 215 |  |  |  |  | 215 |  |  |  | 220 |
| Leu | Leu | Glu | Leu | Lys | Arg | Thr | Gly | Arg | Tyr | Asp | Ala | Phe | Val | Thr |
|  |  |  | 225 |  |  |  |  | 230 |  |  |  | 235 |
| Thr | His | Asn | Ala | Phe | Ile | Leu | Gly | Asp | Thr | Asp | Asn | Gly | Glu | Arg |
|  |  |  | 240 |  |  |  |  | 245 |  |  |  | 250 |
| Thr | Gly | His | Arg | Ser | Pro | Ser | Phe | Leu | Pro | Trp | His | Arg | Arg | Phe |
|  |  |  | 255 |  |  |  |  | 260 |  |  |  | 265 |
| Leu | Leu | Glu | Phe | Glu | Arg | Ala | Leu | Gln | Ser | Val | Asp | Ala | Ser | Val |
|  |  |  | 270 |  |  |  |  | 275 |  |  |  | 280 |
| Ala | Leu | Pro | Tyr | Trp | Asp | Trp | Ser | Ala | Asp | Arg | Ser | Thr | Arg | Ser |
|  |  |  | 285 |  |  |  |  | 290 |  |  |  | 295 |
| Ser | Leu | Trp | Ala | Pro | Asp | Phe | Leu | Gly | Gly | Thr | Gly | Arg | Ser | Arg |
|  |  |  | 300 |  |  |  |  | 305 |  |  |  | 310 |
| Asp | Gly | Gln | Val | Met | Asp | Gly | Pro | Phe | Ala | Ala | Ser | Ala | Gly | Asn |
|  |  |  | 315 |  |  |  |  | 320 |  |  |  | 325 |
| Trp | Pro | Ile | Asn | Val | Arg | Val | Asp | Gly | Arg | Thr | Phe | Leu | Arg | Arg |
|  |  |  | 330 |  |  |  |  | 335 |  |  |  | 340 |
| Ala | Leu | Gly | Ala | Gly | Val | Ser | Glu | Leu | Pro | Thr | Arg | Ala | Glu | Val |
|  |  |  | 345 |  |  |  |  | 350 |  |  |  | 355 |
| Asp | Ser | Val | Leu | Ala | Met | Ala | Thr | Tyr | Asp | Met | Ala | Pro | Trp | Asn |
|  |  |  | 360 |  |  |  |  | 370 |  |  |  | 375 |
| Ser | Gly | Ser | Asp | Gly | Phe | Arg | Asn | His | Leu | Glu | Gly | Trp | Arg | Gly |
|  |  |  | 380 |  |  |  |  | 385 |  |  |  | 390 |
| Val | Asn | Leu | His | Asn | Arg | Val | His | Val | Trp | Val | Gly | Gly | Gln | Met |
|  |  |  | 395 |  |  |  |  | 400 |  |  |  | 405 |
| Ala | Thr | Gly | Val | Ser | Pro | Asn | Asp | Pro | Val | Phe | Trp | Leu | His | His |
|  |  |  | 410 |  |  |  |  | 415 |  |  |  | 420 |
| Ala | Tyr | Ile | Asp | Lys | Leu | Trp | Ala | Glu | Trp | Gln | Arg | Arg | His | Pro |
|  |  |  | 425 |  |  |  |  | 430 |  |  |  | 435 |

| | | | | | | | | | | | | |
|---|---|---|---|---|---|---|---|---|---|---|---|---|
| Ser | Ser | Pro | Tyr | Leu 440 | Pro | Gly | Gly | Gly | Thr 445 | Pro | Asn | Val | Val | Asp 450 |
| Leu | Asn | Glu | Thr | Met 455 | Lys | Pro | Trp | Asn | Asp 460 | Thr | Thr | Pro | Ala | Ala 465 |
| Leu | Leu | Asp | His | Thr 470 | Arg | His | Tyr | Thr | Phe 475 | Asp | Val | Gly | | |